() United States Patent  
Cho

(10) Patent No.: US 7,090,840 B2  
(45) Date of Patent: Aug. 15, 2006

(54) LACTOBACILLUS PARACASEI SUBSP. PARACASEI STRAIN ANTIBACTERIAL AGAINST HELICOBACTER PYLORI AND ESCHERICHIA COLI 0157:H7

(76) Inventor: Seong-Kun Cho, 203, #441-3 Anyang-dong, Manan-gu, Anyang-si, Kyonggi-do 430-010 (KR)

( * ) Notice: Subject to any disclaimer, the term of this patent is extended or adjusted under 35 U.S.C. 154(b) by 207 days.

(21) Appl. No.: 10/204,883

(22) PCT Filed: Dec. 28, 2001

(86) PCT No.: PCT/KR01/02297

§ 371 (c)(1),  
(2), (4) Date: Aug. 23, 2002

(87) PCT Pub. No.: WO02/053706

PCT Pub. Date: Jul. 11, 2002

(65) Prior Publication Data

US 2003/0138406 A1   Jul. 24, 2003

(30) Foreign Application Priority Data

Dec. 29, 2000  (KR)  .............................. 2000-85232

(51) Int. Cl.  
*A01N 63/00* (2006.01)

(52) U.S. Cl. .................................... 424/93.45; 424/93.1

(58) Field of Classification Search ............ 435/252.9; 424/93.45, 780, 93.1, 439, 93.2; 426/2, 61, 426/41, 72, 583; 514/53, 58, 2  
See application file for complete search history.

(56) References Cited

U.S. PATENT DOCUMENTS 6,025,187 A * 2/2000 Penaud .................... 435/262.5

| | | | | |
|---|---|---|---|---|
| 6,042,728 A | * | 3/2000 | Ito et al. .................... | 210/611 |
| 6,592,863 B1 | * | 7/2003 | Fuchs et al. ............... | 424/93.1 |
| 6,599,504 B1 | * | 7/2003 | Wadstrom et al. ....... | 424/93.45 |
| 6,835,376 B1 | * | 12/2004 | Neeser et al. ............ | 424/93.45 |
| 6,887,465 B1 | * | 5/2005 | Reniero et al. .......... | 424/93.45 |
| 6,887,850 B1 | * | 5/2005 | Fuchs et al. .................... | 514/2 |
| 2003/0049240 A1 | * | 3/2003 | Ballevre et al. ......... | 424/93.45 |

(Continued)

FOREIGN PATENT DOCUMENTS

EP             0852114        *  7/1998

(Continued)

OTHER PUBLICATIONS

Caridi, A, Journal of Industrial Microbiology and Biotechnology, 2002, vol. 29, pp. 303-308.*

(Continued)

*Primary Examiner*—Lynette R. F. Smith  
*Assistant Examiner*—Ginny Allen Portner  
(74) *Attorney, Agent, or Firm*—Dilworth & Barrese LLP.

(57) ABSTRACT

The present invention relates to novel lactic microorganism, method for preparation and uses thereof. Particularly, the present invention relates to novel *Lactobacillus paracasei* strain (*Lactobacillus paracasei* subsp. *paracasei* CSK 01) which is prepared by the process comprising the steps: (1) administering lactic bacteria derived from gastric mucus of pig to patients of gastritis and enteritis; (2) separating lactic bacteria from the patients' feces again after their complete recovery; and (3) identifying the bacteria strain by performing 16S rRNA sequencing and RAPD polymerase chain reaction. The *Lactobacillus* strain of the present invention can attach to and proliferate on gastric and intestinal mucosa, resist to acidic and bilious conditions outstandingly and have excellent antibacterial properties. Therefore, the *Lactobacillus* strain and its antibacterial substance can be utilized widely to develop new drugs, functional food, health promoting additives and the like.

5 Claims, 20 Drawing Sheets

U.S. PATENT DOCUMENTS

| | | | |
|---|---|---|---|
| 2003/0202992 A1* | 10/2003 | Fuchs et al. | 424/283.1 |
| 2005/0019894 A1* | 1/2005 | Park | 435/252.9 |
| 2005/0153019 A1* | 7/2005 | Fuchs et al. | 426/72 |

FOREIGN PATENT DOCUMENTS

| | | | |
|---|---|---|---|
| EP | 1034788 | * | 9/2000 |
| WO | 99/29833 | * | 6/1999 |
| WO | WO 99/29833 | | 6/1999 |
| WO | WO 00/53202 | | 9/2000 |
| WO | WO 00/54788 | | 9/2000 |
| WO | 01/52667 | * | 7/2001 |

OTHER PUBLICATIONS

Claire, Russ, Probiotic cheese, Diary Inducstries International, Jul. 25, 2000.*

Fitzsimons, NA et al, Applied and Environmental Microbiology, vol. 65(8), pp. 3418-3426, Aug. 1999.*

Jin, Li-Zhi et al, Journal of the Science of Food and Agriculture, vol. 80, pp. 619-624, 2000.*

Nemcova, R et al, Berl. Munch Tierarztl. Wochenschr., Jun.-Jul. 1999, vol. 112, (6-7), pp. 225-228, Study of the effect of *Lactobacillus paracasei* and fructooligosaccharides on the faecal microflora in weanling piglets.*

Ward, LJH et al, Letters in Applied Microbiology, vol. 29, pp. 90-92, 1999, Differentiation of *Lactobacillus casei, Lactobacillus paracasei* and *Lactobacillus rhamnosus* by polymerase chain reaction.*

Mori, K et al, International Journal of Systematic Bacteriology, Jan. 1997, vol. 47(1), pp. 54-57.*

Pelletier, C et al, Applied and Environmental Microbiology, May 1997, vol. 63(5), pp. 1725-1731.*

Xanthopoulos, V et al, Journal of Applied Microbiology, vol. 87, pp. 743-749, 1999.*

Gardiner, G et al, Applied and Environmental Microbiology, Jun. 1998, vol. 64 (6), pp. 2192-2199.*

Tilsala-Timisjarvi, A et al, International Journal of Food Microbiology, vol. 35, pp. 49-56, 1997.*

Hessle, C et al, Clin. Exp. Immunol., 1999, vol. 116, pp. 276-282, Lactobacilli from human gastrointesinal mucosa are strong stimulators of IL-12 production.*

Nemocova et al (1997) reference of record.*

Nemocova et al (1999) reference of record.*

Jin et al (Apr. 2000) reference of record.*

Kirjavainen et al (1998) reference of record.*

Ljungh et al, reference of record.*

Ohlson et al, reference of record.*

* cited by examiner

```
-------------------------------------------------------------------------------------------------
ID:      4452      JIWON769(MRS 4DAYS)                          Date of run: 20-MAR-98 21:53:54
Bottle: 15         SAMPLE      (AEROBE)

RT      Area   Ar/Ht Respon    ECL       Name              %    Comment 1           Comment 2
  ------ --------- ----- ------  ------  -----------------  ------  -------------------  ----------------------
   1.394 316126720 0.026  . . .   7.056  SOLVENT PEAK . . . . . .   < min rt
   6.203      1280 0.036  . . .  13.814  . . . . . . . . . . . .
   6.264      1312 0.037  . . .  13.862  . . . . . . . . . . . .
   6.439     11456 0.035  0.978  14.000  14:0 . . . . . . . 10.07  ECL deviates  0.000   Reference -0.002
   9.109       864 0.045  0.941  15.773  16:1 w9c . . . . .  0.73  ECL deviates -0.001
   9.175     11936 0.043  0.940  15.815  Sum In Feature .  10.09   ECL deviates -0.002   16:1 w7c/15 iso 2OH
   9.235      7480 0.042  0.940  15.853  Sum In Feature 4 . . 6.32 ECL deviates  0.006   15:0 ISO 2OH/16:1w7c
   9.320      1608 0.050  0.939  15.906  16:1 w5c . . . . .  1.36  ECL deviates -0.002
   9.467     12248 0.042  0.938  15.999  16:0 . . . . . . . 10.32  ECL deviates -0.001   Reference -0.002
  10.240      1104 0.043  0.932  16.463  ISO 17:1 w5c . . .  0.93  ECL deviates  0.002
  10.296      1656 0.044  0.932  16.497  15:0 3OH . . . . .  1.39  ECL deviates -0.007
  10.782      1424 0.050  0.929  16.789  17:1 w8c . . . . .  1.19  ECL deviates -0.003
  12.354       768 0.046  0.923  17.715  Sum In Feature 6 .  0.64  ECL deviates -0.005   18:2 w6,9c/18:0 ANTE
  12.440     25064 0.046  0.923  17.766  18:1 w9c . . . . . 20.79  ECL deviates -0.003
  12.534     12144 0.060  0.923  17.821  Sum In Feature 7 . 10.07  ECL deviates -0.001   18:1 w7c/w9t/w12t
  12.840      1200 0.054  0.922  18.000  18:0 . . . . . . .  0.99  ECL deviates  0.000   Reference  0.000
  13.171      2832 0.056  . . .  18.194  . . . . . . . . . . . .
  13.309      2088 0.048  . . .  18.275  . . . . . . . . . . . .
  13.890      1072 0.052  . . .  18.615  . . . . . . . . . . . .
  14.311     30400 0.052  0.919  18.862  Sum In Feature 9 . 25.12  ECL deviates  0.004   un 18.858/.846/19cy
  16.190       848 0.055  . . .  19.972  . . . . . . . . . . . .
  16.945       984 0.055  . . .  20.418  . . . . . . . . . . . .  > max rt
 ******     19416 . . . . . .    . . .   SUMMED FEATURE 4 . 16.40  16:1 w7c/15 iso 2OH   15:0 ISO 2OH/16:1w7c
 ******       768 . . . . . .    . . .   SUMMED Feature 6 .  0.64  18:2 w6,9c/18:0 ANTE  18:0 ANTE/18:2 w6,9c
 ******     12144 . . . . . .    . . .   SUMMED FEATURE 7 . 10.07  18:1 w7c/w9t/w12t     18:1 w9c/w12t/w7c
 ******   . . . . . . . . .      . . .   . . . . . . . . . . . .   18:1 w12t/w9t/w7c
 ******     30400 . . . . . .    . . .   SUMMED Feature 9 . 25.12  un 18.846/18.858      un 18.858/.846/19cy
 ******   . . . . . . . . .      . . .   . . . . . . . . . . . .   19:0 CYCLO w10c/un Solvent Ar  Total Area   Named Area   % Named   Total Amnt   nbr Ref   ECL Deviation   Ref ECL Shift
 ----------  ----------   ----------   -------   ----------   -------   -------------   -------------
  316126720     128784      119352      92.68      111256        3          0.003           0.001
-------------------------------------------------------------------------------------------------

TSBA (Rev 3.90) Lactobacillus . . . . . . . . . . . . . . . . . 0.359
                         L. coryniformis . . . . . . . . . . . . . . . . 0.359
                             L. C. coryniformis  . . . . . . . . . . . . 0.359
                         L. buchneri* . . . . . . . . . . . . . . . . .  0.259 (MRSA)
                           L. brevis* . . . . . . . . . . . . . . . . .  0.240 (MRSA)
```

FIG. 5a

BIO-NUMBER : 0 0 0 4 0 2 0 2 6 3 4 0 0 0 4 0 3 0 0 0 0 0
0 0 0 0 0 0 0 0 0 0
BEST ID : LACTOBACILLUS CASEI SS RHAMNOSUS

| | | | | |
|---|---|---|---|---|
| LCB.CAS SS RHAMNO | 0.793 | 1.892 | 0.113 | 0.569 |
| LCB.PCA SS PARACASEI | 0.034 | 2.934 | 0.080 | 1.194 |
| LCB.CAS SS CASEI | 0.034 | 2.934 | 0.113 | 4.512 |

0.246 0.362 0.272 0.295 0.273 0.266 0.300 0.282 0.307 0.673 0.262 0.252
0.309 0.261 0.288 0.273 0.577 0.332 0.388 0.264 0.281 0.251 0.620 0.256
0.675 0.489 0.303 0.261 0.630 0.535 0.445 0.259 0.272 0.312 0.279 0.257
0.276 0.255 0.271 0.359 0.256 0.297 0.467 0.309 0.275 0.279 0.255 0.266
0.290 0.555 0.544 0.254 0.270 0.278 0.285 0.283 0.296 0.269 0.259 0.267
0.274 0.268 0.262 0.260 0.276 0.299 0.282 0.304 0.300 0.254 0.257 0.253
0.276 0.255 0.254 0.256 0.248 0.253 0.252 0.256 0.276 0.255 0.252 0.267
0.278 0.280 0.258 0.271 0.256 0.256 0.253 0.259 0.288 0.253 0.252 0.262

| | | | | | | | | | | | |
|---|---|---|---|---|---|---|---|---|---|---|---|
| 0 | 47 | 11 | 20 | 11 | 8 | 22 | 15 | 25 | 174 | 7 | 2 |
| 26 | 6 | 17 | 11 | 135 | 35 | 58 | 7 | 14 | 2 | 152 | 4 |
| 174 | 99 | 23 | 6 | 156 | 117 | 81 | 5 | 11 | 27 | 13 | 4 |
| 12 | 4 | 10 | 46 | 4 | 21 | 90 | 26 | 12 | 13 | 4 | 8 |
| 18 | 126 | 121 | 3 | 10 | 13 | 16 | 15 | 20 | 9 | 5 | 9 |
| 11 | 9 | 7 | 6 | 12 | 22 | 15 | 24 | 22 | 3 | 4 | 3 |
| 12 | 4 | 3 | 4 | 1 | 3 | 2 | 4 | 12 | 4 | 2 | 9 |
| 13 | 14 | 5 | 10 | 4 | 4 | 3 | 5 | 17 | 3 | 2 | 7 |

BIO-NUMBER : 0 0 0 4 0 2 4 2 6 3 4 0 0 0 4 0 3 0 0 0 0 0
0 0 0 0 0 0 0 0 0 0
BEST ID : LACTOBACILLUS CASEI SS RHAMNOSUS
LCB.CAS SS RHAMNO    0.793    1.892    0.113    0.569
LCB.PCA SS PARACASEI   0.034    2.934    0.080    1.194
LCB.CAS SS CASEI     0.034    2.934    0.113    4.512

0.246 0.362 0.272 0.295 0.273 0.268 0.303 0.283 0.307 0.680 0.265 0.252
0.311 0.262 0.288 0.275 0.577 0.265 0.390 0.265 0.283 0.254 0.622 0.258
0.764 0.492 0.303 0.263 0.632 0.538 0.446 0.262 0.274 0.316 0.283 0.260
0.278 0.258 0.272 0.361 0.257 0.299 0.469 0.311 0.275 0.282 0.256 0.269
0.291 0.559 0.546 0.255 0.271 0.281 0.287 0.284 0.297 0.269 0.260 0.269
0.276 0.271 0.262 0.261 0.277 0.300 0.280 0.304 0.301 0.255 0.257 0.254
0.277 0.257 0.256 0.258 0.249 0.253 0.252 0.257 0.275 0.255 0.252 0.269
0.278 0.281 0.259 0.272 0.256 0.257 0.253 0.258 0.288 0.255 0.253 0.263

| 0 | 47 | 11 | 20 | 11 | 9 | 23 | 15 | 25 | 176 | 8 | 2 |
|---|---|---|---|---|---|---|---|---|---|---|---|
| 26 | 7 | 17 | 12 | 135 | 8 | 59 | 8 | 15 | 3 | 153 | 5 |
| 211 | 100 | 23 | 7 | 157 | 119 | 81 | 7 | 11 | 28 | 15 | 6 |
| 13 | 5 | 11 | 47 | 4 | 22 | 91 | 26 | 12 | 15 | 4 | 9 |
| 18 | 127 | 122 | 4 | 10 | 14 | 17 | 15 | 21 | 9 | 6 | 9 |
| 12 | 10 | 7 | 6 | 13 | 22 | 14 | 24 | 22 | 4 | 4 | 3 |
| 13 | 4 | 4 | 5 | 1 | 3 | 2 | 4 | 12 | 4 | 2 | 9 |
| 13 | 14 | 5 | 11 | 4 | 4 | 3 | 5 | 17 | 4 | 3 | 7 |

```
BIO-NUMBER : 0 0 0 4 0 2 4 2 7 3 4 4 0 1 6 0 7 0 0 0 3
0 0 0 0 1 0 0 0 0 0
BEST ID : LACTOBACILLUS PARACASEI SS PARACASEI
LCB.PCA SS PARACASEI    0.544   4.710   0.080   0.819
LCB.CAS SS RHAMNO       0.141   5.154   0.344   1.556
LCB.CAS SS CASEI        0.000   7.345   0.344   3.256
```

0.222 0.297 0.261 0.275 0.258 0.259 0.272 0.304 0.312 2.336 0.253 0.221
0.298 0.266 0.351 0.328 2.318 0.309 1.116 0.264 0.277 0.249 2.366 0.248
2.429 1.958 1.193 0.274 1.296 2.589 2.608 0.259 0.278 1.123 0.262 0.260
0.289 0.251 0.268 0.347 0.258 0.921 1.498 1.272 0.272 0.267 0.254 0.266
0.457 2.356 2.559 0.254 0.282 0.287 0.291 0.312 0.295 0.283 0.269 0.245
0.295 0.272 0.271 0.266 0.707 0.935 0.288 0.339 0.324 0.263 0.260 0.245
0.283 0.260 0.261 0.267 0.255 0.268 0.262 0.261 0.350 0.263 0.260 0.266
0.281 0.278 0.263 0.280 0.260 0.263 0.246 0.266 0.300 0.259 0.257 0.259

|   0 |  34 |   18 |  24 |  16 |  17 |   23 |  37 |  41 | 952 |  14 |   0 |
|----:|----:|-----:|----:|----:|----:|-----:|----:|----:|----:|----:|----:|
|  34 |  20 |   58 |  48 | 944 |  39 |  403 |  19 |  25 |  12 | 966 |  12 |
| 994 | 782 |  437 |  23 | 484 |1066 | 1075 |  17 |  25 | 406 |  18 |  17 |
|  30 |  13 |   21 |  56 |  16 | 315 |  575 | 473 |  23 |  20 |  14 |  20 |
| 106 | 961 | 1053 |  14 |  27 |  29 |   31 |  41 |  33 |  27 |  21 |  10 |
|  33 |  23 |   22 |  20 | 218 | 321 |   30 |  53 |  46 |  18 |  17 |  10 |
|  27 |  17 |   18 |  20 |  15 |  21 |   18 |  18 |  58 |  18 |  17 |  20 |
|  27 |  25 |   18 |  26 |  17 |  18 |   11 |  20 |  35 |  17 |  16 |  17 |

```
BIO-NUMBER : 0 0 0 4 1 3 4 2 7 3 4 4 0 1 6 0 7 0 0 0 0 3
              0 0 0 0 1 0 0 0 0 0
```

BEST ID : LACTOBACILLUS PARACASEI SS PARACASEI

| | | | | |
|---|---|---|---|---|
| LCB.PCA SS PARACASEI | 0.496 | 5.710 | 0.080 | 0.819 |
| LCB.CAS SS RHAMNO | 0.128 | 6.154 | 0.344 | 1.556 |
| LCB.CAS SS CASEI | 0.000 | 8.345 | 0.344 | 3.256 |

GGTTCTCCTACGGCTACCTTGTTACGACTTCACCTAATCATTGTCCCACCTTAGACGGCTCGCTCCCTAAAAGGGTTACGCCA
CCGGCTTCGGGTGTTACAAACTCTCATGGTGTGACGGGCGGTGTGTACAAGGCCCGGGAACGTATTCACCGCGGCGTGCTGATCC
GCGATTACTAGCGATTCCGACTTCGTGTAGGGAGTTGCAGCCTACAGTCCGAACTGAGAATGGCTTTAAGAGATTAGCTTGACC
TCGCGGTCTCGCAACTCGTTGTGTACCATCCATTGTAGCACGTGTGTAGCCCAGGTCATAAGGGGCATGATGATTTGACGTCATCCC
CACCTTCCTCCGGTTTGTCACCGGCAGTCTTACTAGAGTGCCCAACTAAATGTGGCAACTAGTCATAAGGGTTGCGCTCGTTGC
GGGACTTAACCCAACATCTCAGACAGCAGCTGACGACAACCATGCACCACCTGTCATTTGCCCCGAAGGGGAAACCTGATCT
CTCAGGTGATCAAAAGATGTCAAGACCTGGTAAGGTTCTTCGCGTTGCTTCGAATTAAACCACATGCTCCACCGCTTGTGCGGGC
CCCGTCAATTCCTTGAGTTTCAACCTTGGCGGTCGTCACCCTTGCCTACTCCCCAGGCGGAATGCTTAATGCGTTAGCTGCGCACTGAAGGGCG
GAAACCCCTCCAACACCTAGCATTCATCGTTTACGGCATGGACTACCAGGGTATCTAATCCTGTTCGCTACCCATGCTTCGAGCC
TCAGGGTCAGTTACAGACCAGACAGCCGCCTTCGCCACTGGTGTTCTTCCATATATCTACGCATTTCACCGCTACACATGGAGTT
CCACTGTCTCTGTCTCGCACTCAAGTTTCCCAGTTCCGATGCCGTTCGGGCTTTCACATCAGACTTAAAAA
ACCGGCTGCGCTCGCTTTACGCCCAATAAATCCGGATAACGCTTGCCACCTAGTATTACCGGGCTGCTGGCACGTAGTTAGCC
GTGGCTTTCTGGTTGGATACGGTCACGCGTCACAGCGACAACAGTTACTCTGCGACCATTCTCTCCAACAACAGAGTTTACGACCCGAA
AGCCTTCTTCACTCACGCGGCGTGCTGCATCAGAGACTTGGTGTCATTGTGGAAGATTCCCTACTGCTGCCTCCGTAGGAGTTG
GGCCGTGTCTCAGTCCCAATGGCCGATCAACCCTCAGTTCGGCTACGTATCATCGCCTTGGTGAGCCATTACCTCACCAACT
AGCTAATACGCCGCGGGTCCATCCAAAAGCGATAGCTTACGCCATCTTTCAGCCAAGAACCATGCGGTTCTTGGATCTATGCGGT
ATTAGCATCGTTTCCAAATGTTATCCCCACTTAAGGGCAGGTTACCCACGTGTTACTCACCGTCCGCCACTCGTTCCATGTT
GAATCTCAGTGCAAGCACCGATCATCAACGAGAACTCGTTCGACTTGCATGTATTAGGCACGCCGCCAGCGTTCATC

FIG. 7

| Sequences producing significant alignments: | Score (bits) | E Value |
|---|---|---|
| dbj\|D79212.1\|LBA16SRRNA  Lactobacillus paracasei gene for 16... | 2970 | 0.0 |
| dbj\|D86517.1\|D86517  Lactobacillus casei DNA for 16S ribosom... | 2970 | 0.0 |
| dbj\|D16548.1\|D16548  Lactobacillus casei DNA for 16S rRNA | 2938 | 0.0 |
| dbj\|D16549.1\|D16549  Lactobacillus casei DNA for 16S rRNA | 2922 | 0.0 |
| gb\|AF243147.1\|AF243147  Lactobacillus paracasei subsp. parac... | 2920 | 0.0 |
| dbj\|D16550.1\|D16550  Lactobacillus casei DNA for 16S rRNA | 2914 | 0.0 |
| emb\|AJ272201.1\|LCA272201  Lactobacillus casei subsp. casei p... | 2892 | 0.0 |
| dbj\|D86518.1\|D86518  Lactobacillus casei DNA for 16S ribosom... | 2882 | 0.0 |
| dbj\|D86516.1\|D86516  Lactobacillus zeae DNA for 16S ribosoma... | 2878 | 0.0 |
| gb\|AF243168.1\|AF243168  Lactobacillus paracasei subsp. parac... | 2870 | 0.0 |
| dbj\|D16551.1\|D16551  Lactobacillus casei DNA for 16S rRNA | 2861 | 0.0 |
| dbj\|D16552.1\|D16552  Lactobacillus casei DNA for 16S rRNA | 2795 | 0.0 |
| gb\|M23928.1\|LBARRNAB  L.casei small subunit ribosomal RNA | 2791 | 0.0 |
| gb\|AF243146.1\|AF243146  Lactobacillus rhamnosus strain F11 1... | 2777 | 0.0 |
| emb\|AJ271854.1\|LPA271854  Lactobacillus paracasei partial 16... | 2706 | 0.0 |
| gb\|M58815.1\|LBARR16SN  Lactobacillus casei 16S ribosomal RNA | 2662 | 0.0 |
| emb\|AJ271383.1\|PIN271383  Pediococcus inopinatus 16S rRNA ge... | 2093 | 0.0 |
| dbj\|AB033209.1\|AB033209  Lactobacillus algidus gene for 16S ... | 1955 | 0.0 |
| dbj\|AB024300.1\|AB024300  Lactobacillus kefiri gene for 16S r... | 1945 | 0.0 |
| dbj\|D37785.1\|D37785  Lactobacillus brevis DNA for 16S rRNA | 1927 | 0.0 |
| emb\|X76328.1\|LR16SRRI  L.reuteri (DSM 20016 T) 16S rRNA gene... | 1925 | 0.0 |
| gb\|AF264701.1\|AF264701  Lactobacillus sp. JKD6 16S ribosomal... | 1917 | 0.0 |
| gb\|AF157049.1\|AF157049  Lactobacillus murinus 16S ribosomal ... | 1917 | 0.0 |
| emb\|X76330.1\|LF16SRR  L.fructivorans (DSM 20203 T) 16S rRNA ... | 1911 | 0.0 |
| gb\|M58821.1\|LBARR16SQ  Lactobacillus hilgardii 16S ribosomal... | 1911 | 0.0 |
| gb\|AF090328.1\|AF090328  Lactobacillus brevis 16S ribosomal R... | 1905 | 0.0 |
| dbj\|AB018213.1\|AB018213  Pediococcus acidilactici gene for 1... | 1905 | 0.0 |
| gb\|M58834.1\|PDCRR16SA  Pediococcus pentosaceus 16S ribosomal... | 1903 | 0.0 |
| dbj\|AB016864.1\|AB016864  Lactobacillus sp. gene for 16S rRNA... | 1901 | 0.0 |
| gb\|AF275311.1\|AF275311  Lactobacillus ferintoshensis 16S rib... | 1899 | 0.0 |
| dbj\|D88528.1\|D88528  Pediococcus parvulus DNA for 16S riboso... | 1899 | 0.0 |
| gb\|M58810.1\|LBARR16SI  Lactobacillus brevis 16S ribosomal RNA | 1863 | 0.0 |
| dbj\|AB024299.1\|AB024299  Lactobacillus brevis gene for 16S r... | 1861 | 0.0 |
| emb\|Y19167.1\|LPE19167  Lactobacillus perolens 16S rRNA gene,... | 1854 | 0.0 |
| gb\|M58831.1\|LBARR16SAC  Lactobacillus sharpeae 16S ribosomal... | 1810 | 0.0 |

FIG. 9

```
>dbj|D79212.1|LBA16SRRNA Lactobacillus paracasei gene for 16S rRNA, partial sequence
         Length = 1522

Score = 2970 bits (1498), Expect = 0.0
 Identities = 1518/1522 (99%), Gaps = 2/1522 (0%)
 Strand = Plus / Minus Query:    1  ggttctcctacggctaccttgttacgacttcaccctaatcatttgtccaccttagacgg   60
             ||||||||||||||||||||||||||||||||||||||||||||||||||||||||||||
Sbjct: 1522  ggtctcctacggctaccttgttacgacttcaccctaatcatttgtccaccttagacgg  1463

Query:   61  ctcgctccctaaaagggttacgccaccggcttcgggtgttacaaactctcatggtgtgac  120
             ||||||||||||||||||||||||||||||||||||||||||||||||||||||||||||
Sbjct: 1462  ctcgctccctaaaagggttacgccaccggcttcgggtgttacaaactctcatggtgtgac  1403

Query:  121  gggcggtgtgtacaaggcccgggaacgtattcaccgcggcgtgctgatccgcgattacta  180
             ||||||||||||||||||||||||||||||||||||||||||||||||||||||||||||
Sbjct: 1402  gggcggtgtgtacaaggcccgggaacgtattcaccgcggcgtgctgatccgcgattacta  1343

Query:  181  gcgattccgacttcgtgtaggcgagttgcagcctacagtccgaactgagaatggctttaa  240
             ||||||||||||||||||||||||||||||||||||||||||||||||||||||||||||
Sbjct: 1342  gcgattccgacttcgtgtaggcgagttgcagcctacagtccgaactgagaatggctttaa  1283

Query:  241  gagattagcttgacctcgcggtctcgcaactcgttgtaccatccattgtagcacgtgtgt  300
             ||||||||||||||||||||||||||||||||||||||||||||||||||||||||||||
Sbjct: 1282  gagattagcttgacctcgcggtctcgcaactcgttgtaccatccattgtagcacgtgtgt  1223

Query:  301  agcccaggtcataaggggcatgatgatttgacgtcatccccaccttcctccggtttgtca  360
             ||||||||||||||||||||||||||||||||||||||||||||||||||||||||||||
Sbjct: 1222  agcccaggtcataaggggcatgatgatttgacgtcatccccaccttcctccggtttgtca  1163

Query:  361  ccggcagtcttactagagtgcccaactaaatgctggcaactagtcataagggrtgcgctc  420
             ||||||||||||||||||||||||||||||||||||||||||||||||||||||||||||
Sbjct: 1162  ccggcagtcttactagagtgcccaactaaatgctggcaactagtcataagggrtgcgctc  1103

Query:  421  gttgcgggacttaacccaacatctcacgacacgagctgacgacaaccatgcaccacctgt  480
             ||||||||||||||||||||||||||||||||||||||||||||||||||||||||||||
Sbjct: 1102  gttgcgggacttaacccaacatctcacgacacgagctgacgacaaccatgcaccacctgt  1043

Query:  481  catttgccccgaaggggaaacctgatctctcaggtgatcaaaagatgtcaagacctgg   539
             ||||||||||||||||||||||||||||||||||||||||||||||||||||||||||
Sbjct: 1042  catttgccccgaaggggaaacctgatctctcaggtgatcaaaagatgtcaagacctgg   983

Query:  540  taaggttcttcgcgttgcttcgaattaaaccacatgctccaccgcttgtgcgggcccccg   599
             ||||||||||||||||||||||||||||||||||||||||||||||||||||||||||||
Sbjct:  982  taaggttcttcgcgttgcttcgaattaaaccacatgctccaccgcttgtgcgggcccccg   923

Query:  600  tcaattcctttgagtttcaaccttgcggtcgtactccccaggcggaatgcttaatgcgtt   659
             ||||||||||||||||||||||||||||||||||||||||||||||||||||||||||||
Sbjct:  922  tcaattcctttgagtttcaaccttgcggtcgtactccccaggcggaatgcttaatgcgtt   863

Query:  660  agctgcggcactgaagggcggaaacctccaacacctagcattcatcgttttcggcatgg   719
             |||||||||||||||||||||||||||||||||||||||||||||||||||||||||||
Sbjct:  862  agctgcggcactgaagggcggaaacctccaacacctagcattcatcgttttacggcatgg   803

Query:  720  actaccagggtatctaatcctgttcgctacccatgctttcgagctcagcgtcagttaca   779
             |||||||||||||||||||||||||||||||||||||||||||||||||||||||||||
Sbjct:  802  actaccagggtatctaatcctgttcgctacccatgctttcgagctcagcgtcagttaca   743

Query:  780  gaccagacagccgcctcgccactggtgttcttccatatatctacgcattcaccgctac   839
             |||||||||||||||||||||||||||||||||||||||||||||||||||||||||
Sbjct:  742  gaccagacagccgcctcgccactggtgttcttccatatatctacgcattcaccgctac   683

Query:  840  acatggagttccactgtcctcatctgcactcaagtttcccagtttcgatgcgcttcctc   899
             ||||||||||||||||||||||||||||||||||||||||||||||||||||||||||
Sbjct:  682  acatggagttccactgtcctcatctgcactcaagtttcccagtttcgatgcgcttcctc   623

Query:  900  ggttaagccgagggctttcacatcagacttaaaaaaccgcctgcgctcgctttacgccca   959
             ||||||||||||||||||||||||||||||||||||||||||||||||||||||||||||
Sbjct:  622  ggttaagccgagggctttcacatcagacttaaaaaaccgcctgcgctcgctttacgccca   563

Query:  960  ataaatccggataacgcttgccacctacgtattaccgcggctgctggcacgtagttagcc  1019
             ||||||||||||||||||||||||||||||||||||||||||||||||||||||||||||
Sbjct:  562  ataaatccggataacgcttgccacctacgtattaccgcggctgctggcacgtagttagcc   503

Query: 1020  gtggctttctggttggataccgtcacgccgacaacagttactctgccgaccattcttctc  1079
             ||||||||||||||||||||||||||||||||||||||||||||||||||||||||||||
Sbjct:  502  gtggctttctggttggataccgtcacgccgacaacagttactctgccgaccattcttctc   443

Query: 1080  caacaacagagttttacgacccgaaagccttcttcactcacgcggcgttgctccatcaga  1138
             ||||||||||||||||||||||||||||||||||||||||||||||||||||||||||||
Sbjct:  442  caacaacagagttttacgacccgaaagccttcttcactcacgcggcgttgctccatcaga   383

Query: 1139  cttgcgtccattgtggaagattccctactgctgcctcccgtaggagtttgggccgtgtct  1198
             ||||||||||||||||||||||||||||||||||||||||||||||||||||||||||||
Sbjct:  382  cttgcgtccattgtggaagattccctactgctgcctcccgtaggagtttgggccgtgtct   323

Query: 1199  cagtcccaatgtggccgatcaacctctcagttcggctacgtatcatcgccttggtgagcc  1258
             ||||||||||||||||||||||||||||||||||||||||||||||||||||||||||||
Sbjct:  322  cagtcccaatgtggccgatcaacctctcagttcggctacgtatcatcgccttggtgagcc   263

Query: 1259  attacctcaccaactagctaatacgccgcgggtccatccaaaagcgatagcttacgccat  1318
             ||||||||||||||||||||||||||||||||||||||||||||||||||||||||||||
Sbjct:  262  attacctcaccaactagctaatacgccgcgggtccatccaaaagcgatagcttacgccat   203

Query: 1319  ctttcagccaagaaccatgcggttcttggatctatgcggtattagcatctgtttccaaat  1378
             ||||||||||||||||||||||||||||||||||||||||||||||||||||||||||||
Sbjct:  202  ctttcagccaagaaccatgcggttcttggatctatgcggtattagcatctgtttccaaat   143

Query: 1379  gttatccccacttaagggcaggttacccacgtgttactcacccgtccgccactcgttcc  1438
             |||||||||||||||||||||||||||||||||||||||||||||||||||||||||||
Sbjct:  142  gttatccccacttaagggcaggttacccacgtgttactcacccgtccgccactcgttcc    83

Query: 1439  atgttgaatctcggtgcaagcaccgatcatcaacgagaactcgttcgacttgcatgtatt  1498
             ||||||||||||||||||||||||||||||||||||||||||||||||||||||||||||
Sbjct:   82  atgttgaatctcggtgcaagcaccgatcatcaacgagaactcgttcgacttgcatgtatt    23

Query: 1499  aggcacgccgccagcgttcatc  1520
             ||||||||||||||||||||||
Sbjct:   22  aggcacgccgccagcgttcatc     1
```

Colonies No. of Isolated strain after mixed culture isolated and
E. coli in 10% skim milk
1,2,3 : Colonies No. of Isolated strain
4,5,6 : Colonies No. of E. coli

SEQUENCE LISTING

<160> NUMBER OF SEQ ID NOS: 5

<210> SEQ ID NO 1
<211> LENGTH: 24
<212> TYPE: DNA
<213> ORGANISM: Sense primer F9

<400> SEQUENCE: 1
cccactgctg cctcccgtag gagt                                    24

<210> SEQ ID NO 2
<211> LENGTH: 18
<212> TYPE: DNA
<213> ORGANISM: Antisence primer 1542R

<400> SEQUENCE: 2
caccgagatt caacatgg                                           18

<210> SEQ ID NO 3
<211> LENGTH: 1522
<212> TYPE: DNA
<213> ORGANISM: Lactobacillus paracasei subsp. paracasei CSK 01

<400> SEQUENCE: 3
ggttctccta cggctacctt gttacgactt caccctaatc atttgtccca ccttagacgg     60
ctcgctccct aaaagggtta cgccaccggc ttcgggtgtt acaaactctc atggtgtgac    120
gggcggtgtg tacaaggccc gggaacgtat tcaccgcggc gtgctgatcc gcgattacta    180
gcgattccga cttcgtgtag gcgagttgca gcctacagtc cgaactgaga atggctttaa    240
gagattagct tgacctcgcg gtctcgcaac tcgttgtacc atccattgta gcacgtgtgt    300
agcccaggtc ataagggca tgatgatttg acgtcatccc caccttcctc cggtttgtca    360

-continued

```
ccggcagtct tactagagtg cccaactaaa tgctggcaac tagtcataag ggttgcgctc      420
gttgcgggac ttaacccaac atctcacgac acgagctgac gacaaccatg caccacctgt      480
cattttgccc ccgaagggga aacctgatct ctcaggtgat caaaagatgt caagacctgg      540
taaggttctt cgcgttgctt cgaattaaac cacatgctcc accgcttgtg cgggcccccg      600
tcaattcctt tgagtttcaa ccttgcggtc gtactcccca ggcggaatgc ttaatgcgtt      660
agctgcggca ctgaagggcg gaaaccctcc aacacctagc attcatcgtt tacggcatgg      720
actaccaggg tatctaatcc tgttcgctac ccatgctttc gagcctcagc gtcagttaca      780
gaccagacag ccgccttcgc cactggtgtt cttccatata tctacgcatt tcaccgctac      840
acatggagtt ccactgtcct cgtctgcact caagtttccc agtttccgat gcgcttcctc      900
ggttaagccg agggctttca catcagactt aaaaaaccgc ctgcgctcgc tttacgccca      960
ataaatccgg ataacgcttg ccacctacgt attaccgcgg ctgctggcac gtagttagcc     1020
gtggctttct ggttggatac cgtcacgccg acaacagtta ctctgccgac cattcttctc     1080
caacaacaga gttttacgac ccgaaagcct tcttcactca cgcggcgttg ctccatcaga     1140
cttgcgtcca ttgtggaaga ttccctactg ctgcctcccg taggagtttg ggccgtgtct     1200
cagtcccaat gtggccgatc aacctctcag ttcggctacg tatcatcgcc ttggtgagcc     1260
attacctcac caactagcta atacgccgcg ggtccatcca aaagcgatag cttacgccat     1320
ctttcagcca agaaccatgc ggttcttgga tctatgcggt attagcatct gtttccaaat     1380
gttatccccc acttaagggc aggttaccca cgtgttactc acccgtccgc cactcgttcc     1440
atgttgaatc tcagtgcaag caccgatcat caacgagaac tcgttcgact tgcatgtatt     1500
aggcacgccg ccagcgttca tc                                              1522
```

```
<210> SEQ ID NO 4
<211> LENGTH: 10
<212> TYPE: DNA
<213> ORGANISM: RP primer

<400> SEQUENCE: 4
cagcacccac                                                              10

<210> SEQ ID NO 5
<211> LENGTH: 10
<212> TYPE: DNA
<213> ORGANISM: CRA25 primer

<400> SEQUENCE: 5
aacgcgcaac                                                              10
```

LACTOBACILLUS PARACASEI SUBSP. PARACASEI STRAIN ANTIBACTERIAL AGAINST HELICOBACTER PYLORI AND ESCHERICHIA COLI 0157:H7

CROSS REFERENCE TO RELATED APPLICATIONS

The present application is a section 371 application of PCT International Application No. PCT/KR01/02297, filed Dec. 28, 2001, which claims priority of Korean Application No. 2000/85232, filed Dec. 29, 2000.

TECHNICAL FIELD

The present invention relates to a novel lactic microorganism, its antibacterial substance and methods for preparation thereof. Particularly, the present invention relates to a novel *Lactobacillus paracasei* strain (*Lactobacillus paracasei* subsp. *paracasei* CSK 01) which is prepared by the process comprising the steps: (1) administering lactic bacteria derived from gastric mucus of pig to patients of gastritis and enteritis; (2) separating lactic bacteria from the patients' feces again after their complete recovery; and (3) identifying the bacterial strain by performing 16S rRNA sequencing and RAPD polymerase chain reaction. The *Lactobacillus* strain of the present invention can attach to and proliferate on gastric and intestinal mucosa, resist to acidic and bilious conditions outstandingly and have excellent antibacterial properties and thus can be utilized widely to develop new drugs, functional food, health promoting additives and the like.

BACKGROUND ART

Generally, *Lactobacillus* sp. has a high affinity for epithelial cells of alimentary organs which contain a lot of lectin material. Thus, lactic bacteria coming from outer environment to inner body are prone to attach to and proliferate on this region. Also, the lactic bacteria which are settled habitually in the inner body make colonies onto this affiliated surface.

Various kinds of *Lactobacillus* sp. inhabit aboriginally epithelial cells and make symbiosis to survive mutually, which gives host animals functional benefits consistently. Especially, each species plays a different role and thus has a peculiar function of probiotics, for example A bacterium strain makes colonies, B strain secretes antibacterial substance, C strain secretes highly acidic lactates, D strain helps digestive activities and the like.

Presently, researches about *Lactobacillus* sp. strains described above have been carried out internationally with a lot of competition and thus the lactic bacteria have been applied to various fields practically. Unfortunately, all the functional *Lactobacillus* sp. strains obtained from the researches are derived from gut, feces, food, raw food material and so on. Therefore, the *Lactobacillus* sp. strains are almost killed by gastric acids when prepared with food and eaten although they had an affinity to small and large intestine. Hence the lactic bacteria have problems to be solved for their application and efficacies.

DISCLOSURE OF INVENTION

To overcome the foregoing and other disadvantages, the inventors of the present invention have tried to obtain new lactic bacterial strain which can attach excellently onto gastric and intestinal muci, multiply well and resist to acids, bilis and bacteria. Concretely, we have separated a *Lactobacillus paracasei* strain from recovered patient's feces after administering lactic bacteria derived from gastric mucous of pig to the patients of gastritis and enteritis and then examined morphological, physiological and cultivational properties of the *Lactobacillus paracasei* strain. As a result, the bacterial strain of the present invention was confirmed to be a new *Lactobacillus paracasei* subsp. *paracasei* strain.

The object of the present invention is to provide a new *Lactobacillus paracasei* strain which has an antibacterial property. Particularly, the present invention provides *Lactobacillus paracasei* subsp. *paracasei* CSK 01 strain (accession number: KCTC 0907 BP) which is antibacterial against *Helicobacter pylori* and *Escherichia coli* 0157:H7.

Another object of the present invention is to provide the *Lactobacillus paracasei* subsp. *paracasei* CSK 01 strain which is resistant to acids and bilis and can attach to and proliferate on gastric mucus and intestinal mucus.

Another object of the present invention is to provide a process for preparing *Lactobacillus paracasei* subsp. *paracasei* strain, which comprises the steps as follows: (1) administering lactic bacteria derived from gastric mucus of pig to the patients of gastritis and enteritis; (2) separating lactic bacteria from the patients' feces again after their complete recovery; and (3) identifying the bacterial strain by performing 16S rRNA sequencing and RAPD polymerase chain reaction.

Another object of the present invention is to provide an antibacterial substance which is separated from *Lactobacillus paracasei* subsp. *paracasei* strain and kills or suppresses the proliferation of *Helicobacter pylori* and *Escherichia coli* 0157:H7.

Another object of the present invention is to provide food compositions containing the *Lactobacillus* strain as an effective component, which has functions of preventing and treating gastritis, gastric ulcer and duodenitis induced by *Helicobacter pylori* and enteritis, colitis and rectitis induced by *Escherichia coli* and other intestinal pathological bacterial.

The other object of the present invention is to provide pharmaceutical compositions containing the *Lactobacillus* strain as an effective component, which has functions of preventing and treating gastritis, gastric ulcer and duodenitis induced by *Helicobacter pylori* and enteritis, colitis and rectitis induced by *Escherichia coli* and other intestinal pathological bacteria.

Further objects and advantages of the present invention will appear hereinafter.

BRIEF DESCRIPTION OF THE DRAWINGS

The above and other objects, features and other advantages of the present invention will be more clearly understood from the following detailed description taken in conjunction with the accompanying drawings, in which;

FIG. 2 depicts the analysis of glycolysis with API KIT 50 CHL in said lactic bacterium of the present invention;

FIG. 4 depicts fatty acid compositions of said lactic bacterium which are analyzed with the automated gas chromatography;

Figure 5D:
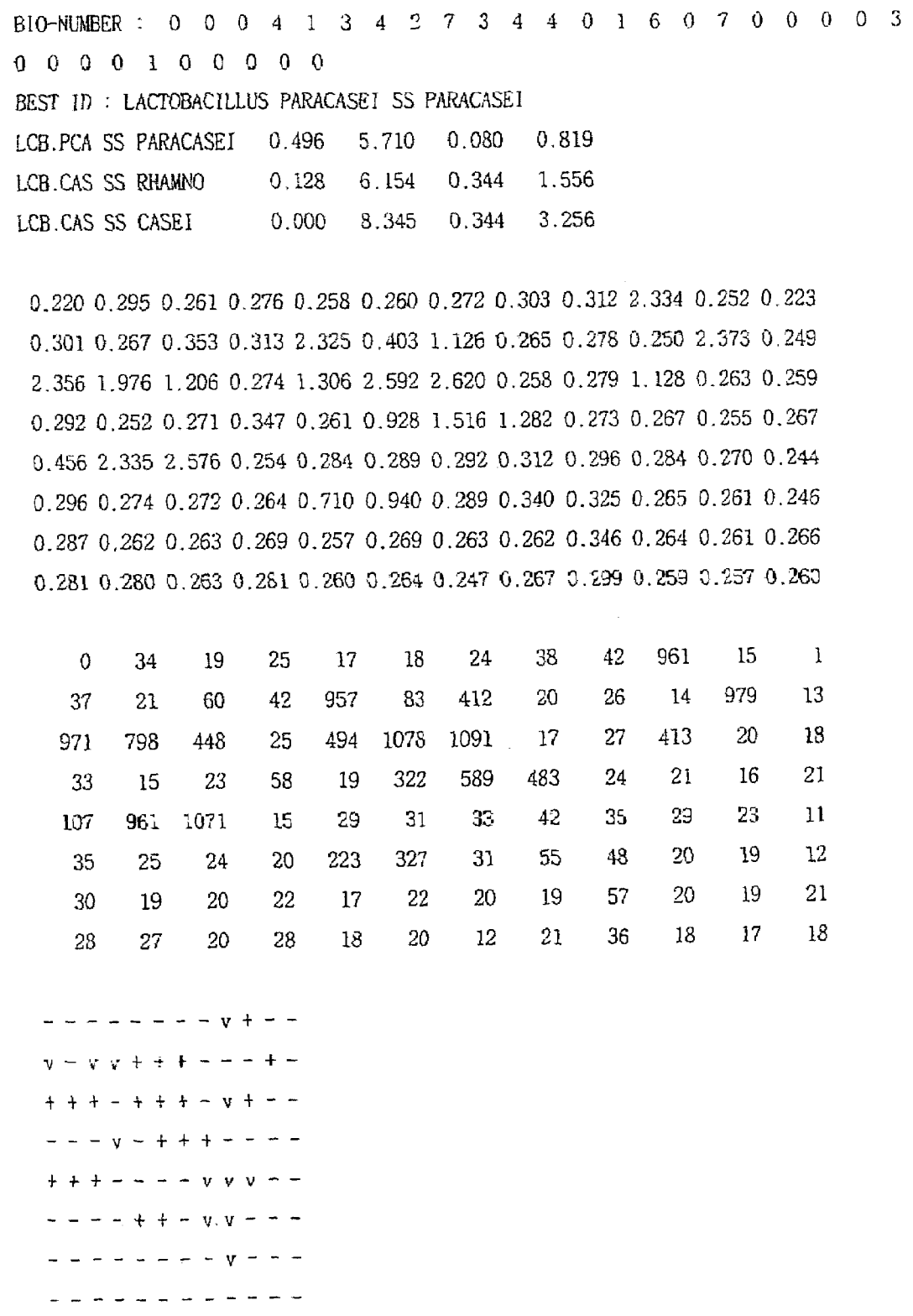

FIG. 5a, FIG. 5b, FIG. 5c and FIG. 5d depict the analysis of 95 carbon sources with the metabolic fingerprint by using the Biolog GP microplate (Biolog Cat. #1004) of said lactic bacterium;

FIG. 6 depicts the nucleotide sequence (SEQ ID NO:3) of 16S DNA in the lactic bacterium of the present invention;

FIG. 7 depicts the BLAST results which are examined by the 16S rRNA sequencing of said lactic bacterium;

FIG. 9 depicts the nucleotide sequence analysis of said lactic bacterium (SEQ ID NO:3) and *Lactobacillus paracasei* subsp. *paracasei* JCM 8130;

BEST MODE FOR CARRYING OUT THE INVENTION

Figure 1A:
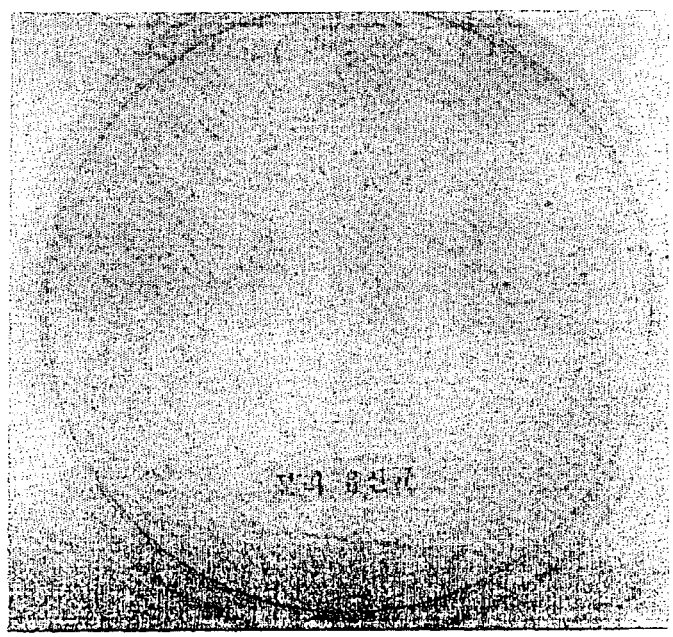
FIG. 1a and FIG. 1b depicts the photograph of Gram-stained lactic bacterium (*Lactobacillus paracasei* subsp. *paracasei* CSK 01 strain) in accordance with the present invention.

The present invention provides a *Lactobacillus paracasei* subsp. *paracasei* strain which has an excellent antibacterial property. Preferably, the *Lactobacillus paracasei* subsp. *paracasei* strain of the present invention is against *Helicobacter pylori* and *Escherichia coli* 0157:H7.

In order to obtain the lactic bacterium, the present invention provides a method for preparation which comprises the following steps; (1) administering lactic bacteria derived from porcine gastric mucus to patients of gastritis and enteritis; and (2) separating lactic bacteria again from the patients' feces after they recover completely. Then, the lactic bacterium of the present invention is examined by performing (1) glycolytic analysis with the API KIT 50 CHL, (2) analysis of cellular fatty acid compositions, (3) analysis of carbon sources usages with the metabolic fingerprint and the like. As a result, the lactic bacterium has been identified to be *Lactobacillus paracasei* subsp. *paracasei* or *Lactobacillus rhamnosus*.

In addition, the *Lactobacillus* sp. strain of the present invention is compared with standard strains by performing the 16S rRNA sequence analysis in order to verify the bacterial strain exactly. Also, the RAPD polymerase chain reaction (PCR) is accomplished to compare the result with that of conventional strains.

Concretely, the strain is confirmed to belong to *Lactobacillus paracasei* subsp. *paracasei* with more than 99.9% of accuracy by using the 16S rRNA sequencing and the BLAST analysis of nucleotide sequences. Besides, approximate 300 bp fragments are discovered both in the strain of the present invention and in the standard *Lactobacillus paracasei* subsp. *paracasei* similarly when the PCR is performed with specific primers for the *Lactobacillus paracasei* group, which confirms the CSK 01 strain of the present invention to be a *Lactobacillus paracasei* subsp. *paracasei*.

On the other hand, the CSK 01 strain of the present invention shows some differences from *Lactobacillus paracasei* subsp. *paracasei* JCM 8130 strain when the results of 16S rDNA sequencing are compared as follows.

Base #861 in CSK 01 strain, G; in JCM 8130 strain, T;

Base #1451 : in CSK 01 strain, A; in JCM 8130 strain,

In addition, when the polymerase chain reaction (PCR) is performed by using RP primer specific for *L. paracasei* sp., approximate 850 bp fragments are common both in the experimental strain and in the standard strain but other bands are different each other. Then, when the PCR is accomplished by using CRA25 primer specific for *L. paracasei* sp., about 980 bp and 550 bp fragments are found in the CSK 01 strain, but the standard strain has inconsistent band patterns. Therefore, the CSK 01 strain is clarified to have its specific characteristics.

In order to verify the safety of the bacterial strain, the culture broth of the strain ($5 \times 10^{9 cfu}$/ml) is injected orally into experimental mice (Balb/c) in the amount of 0.3 ml and its twice 0.6 ml, once a day for 10 days and examined the safeties for 2 months. As a result, the experimental group enables health to be sustained in the naked eye and all the organs maintain normal appearances. Precisely, digestive organs including gastric mucus and small intestinal mucus are similar to those of the standard group.

In addition, the present invention provides a *Lactobacillus paracasei* subsp. *paracasei* strain which is resistant to acidic conditions.

Concretely, after 10% skim milk is adjusted in the pH range of 1.0~4.0 by adding HCl, the bacterial strain of the present invention is inoculated and cultivated for 2 days and 4 days respectively. As a result, the strain is confirmed to be resistant to acidic conditions since it can proliferate even in pH 1.5. As a reference, in the CSK 01 strain, less than $10^{1 cfu}$/ml of cells are separated at pH 1.5 and $10^{4 \sim 5 cfu}$/ml of cells at pH 2.0.

In addition, the present invention provides a *Lactobacillus paracasei* subsp. *paracasei* strain which is resistant to bilis outstandingly.

Concretely, after 10% skim milk is adjusted by adding porcine bilis to become 4.0~4.5%, the bacterial strain of the present invention is inoculated and cultivated for 2 days and 4 days respectively. As a result, the strain is confirmed to be resistant to bile acidic conditions since it can proliferate even in 4.5%. As a reference, in the CSK 01 strain, less than $10^{2 \sim 3 cfu}$/ml of cells are separated in the range of 4.0~4.5%.

In addition, the present invention provides a *Lactobacillus paracasei* subsp. *paracasei* strain which can attach and proliferate onto gastric mucus.

Concretely, the experimental mice are administered orally with 0.3 ml of the culture broth once a day for 10 days and after 2 months 1 g of gastric mucus is cut so as to separate $7\times10^{8cfu}$/g of cells. As a result, the strain is confirmed to attach to and proliferate on gastric mucus innumerably through the electron microscopic observation.

In addition, the present invention provides a *Lactobacillus paracasei* subsp. *paracasei* strain which can attach and proliferate onto small intestinal mucus.

Concretely, the experimental mice are administered orally with 0.3 ml ($7\times10^{9cfu}$/ml) of the culture broth once a day for 10 days and after 2 months 1 g of small intestinal mucus is cut so as to separate $7\times10^{6cfu}$/g of cells. As a result, the strain is confirmed to attach to and proliferate on small intestinal mucus innumerably through the electron microscopic observation.

In addition, the present invention provides a *Lactobacillus paracasei* subsp. *paracasei* strain which can kill *Helicobacter pyroli*.

Concretely, the experimental mice are administered orally with 0.3 ml of *Helicobacter pyroli* culture broth once a day for 5 days and after 3 days of the infection, re-injected orally with 0.3 ml culture broth of the CSK 01 strain once a day for 10 days. As a result, *Helicobacter pyroli* is not separated on the gastric mucus and only the CSK 01 strain is recovered. Thus through the electron microscopic observation, the CSK 01 strain is confirmed to be scattered onto the gastric mucus innumerably.

In addition, the present invention provides a *Lactobacillus paracasei* subsp. *paracasei* strain which can kill and prevent the proliferation of *Escherichia coli*.

Concretely, the experimental mice are administered orally with 0.3 ml of *E. coli* culture broth once a day for 5 days and after 3 days of the infection, re-injected orally with 0.3 ml culture broth of the CSK 01 strain once a day for 10 days. As a result, after 2 months *E. coli* is not separated on the small intestinal mucus and only the CSK 01 strain is recovered. Thus the strain is confirmed to scatter onto the small intestinal mucus innumerably through the electron microscopic observation.

At that time, *Helicobacter pylori* is administered in $7\times10^{9cfu}$/ml of concentration and *Escherichia coli* 0157:H7 is administered in $3\times10^{9cfu}$/ml once a day for 5 days and after 3 days, *Helicobacter pylori* is infected in $7\times10^{7cfu}$/ml onto gastric mucus of mice and *Escherichia coli* 0157:H7 is infected in $7\times10^{4cfu}$/ml onto small intestinal mucus. Then, infected mice are re-injected with the culture broth of the CSK 01 strain in $5\times10^{9cfu}$/ml once a day for 10 days in 0.3 and after 2 months, only the CSK 01 strain is separated with $7\times10^{9cfu}$/gl of gastric mucus and $4\times10^{6cfu}$/g of small intestinal mucus even through *Helicobacter pylori* and *Escherichia coli* are not found.

Besides, 2 culture broths of the CSK 01 strain and *E. coli* are adjusted to the same numbers of cells, inoculated together into 10% skim milk and cultivated for 5 days. As a result, the pattern of cell proliferation is examined that *Escherichia coli* is killed completely within 70 hours but the CSK 01 strain is not affected any the presence of *E. coli* so as to proliferate continuously.

Therefore, the strains obtained above are named with *Lactobacillus paracasei* subsp. *paracasei* CSK 01 and have been deposited with International Deposit Organization, the Korean Collection for Type Cultures (KCTC) of the Korean Research Institute of Bioscience and Biotechnology (KRIBB), #52, Oun-dong, Yusong-ku, Taejon 305–333, Republic of Korea on Dec. 8, 2000, and identified as KCTC accession numbers, KCTC 0907 BP.

The present invention provides an antibacterial substance which is separated from *Lactobacillus paracasei* subsp. *paracasei*-strain and kills or suppresses the proliferation of *Helicobacter pylori* and *Escherichia coli* 0157:H7.

Concretely, the culture broth of *Helicobacter pylori* is smeared on the surface of plate and the disk absorbing the antibacterial substance of the CSK 01 strain is placed onto the center of plate. Then *Helicobacter pylori* is cultivated in the anaerobic condition and examined to be killed around the disk region. In addition, the CKS 01 strain is cultivated with *Escherichia coli* in order to investigate the killing effect of *E. coli* and after 40 hours, *E. coli* dies remarkably.

The present invention provides food compositions including the *Lactobacillus* strain or the antibacterial substance as an effective component, which is functional for preventing and treating gastritis, gastric ulcer and duodenitis induced by *Helicobacter pylori* and enteritis, colitis and rectitis induced by *Escherichia coli* and other intestinal pathological bacteria.

The present invention provides pharmaceutical compositions including the *Lactobacillus* strain or the antibacterial substance as an effective component, which is functional for preventing and treating gastritis, gastric ulcer and duodenitis induced by *Helicobacter pylori* and enteritis, colitis and rectitis induced by *Escherichia coli* and other intestinal pathological bacterial.

In addition, the bacterial strain and the antibacterial substance of the present invention can be utilized as an effective component of functional food such as various kinds of liquid product from lactic fermented milk, various kinds of powder product from live lactic bacteria and inactivated lactic bacteria, various kinds of ice product adding live lactic bacteria and inactivated lactic bacteria, various cheese products of lactic fermented bacteria, various kinds of beverage adding live lactic bacteria and inactivated lactic bacteria, various kinds of beverage and ice product adding extracts of lactic bacterial extracts and the like.

In addition, the *Lactobacillus* sp. strain of the present invention and the antibacterial substance can be utilized as an effective component of ointment which can be applied to skin for treating dermatitis related with *Escherichia coli*. Concretely, various kinds of soluble agent, powder, cream and the like containing live lactic bacteria and/or inactivated lactic bacteria and various kinds of soluble agent, powder, cream and the like containing extracts of the lactic bacteria and/or the purified antibacterial substance.

In addition, the present invention provides pharmaceutical drugs including the *Lactobacillus* strain or the antibacterial substance as an effective component, which can be applied for preventing and treating gastritis, gastric ulcer and duodenitis induced by *Helicobacter pyroli* and enteritis, colitis and rectitis induced by *Escherichia coli* and other intestinal pathological bacteria. Concretely, various kinds of soluble agent, powder, capsule and the like containing live lactic bacteria and/or inactivated lactic bacteria and various kinds of soluble agent, powder, capsule and the like containing extracts of the lactic bacteria and/or the purified antibacterial substance.

The present invention relates to novel *Lactobacillus paracasei* strain (*Lactobacillus paracasei* subsp. *paracasei* CKS 01) which is prepared by the process comprising the steps: (1) separating lactic bacteria from gastric mucosa of pig; (2) administering to gastritis and enteritis patients; and (3) separating from the recovered patients' feces. The *Lactoba-*

*cillus* strain of the present invention have been confirmed to attach and proliferate onto gastric and intestinal mucosa and resist to acidic and bilious conditions outstandingly and have excellent antibacterial properties against *Helicobacter pylori, Escherichia coli* 0157:H7 and the like through identifications of the strain, animal experiments with gastric and small intestinal mucosa, in vivo and in vitro experiments and so on as demonstrated in Examples.

EXAMPLES

Practical and presently preferred embodiments of the present invention are illustrated as shown in the following Examples.

However, it will be appreciated that those skilled in the art, in consideration of this disclosure, may make modifications and improvements within the spirit and scope of the present invention.

Example 1

Separation of Lactic Bacteria from Porcine Stomach

For 10 years (1988~1998), stomachs were obtained from slaughtered pigs (3,270 heads) in butchery markets located in Pusan, Chinju, Suwon, Jeonju, etc. and stored at 4° C. until it be applied for experimental samples.

Then, 1 g of porcine gastric mucosa was immersed on MRS broth and cultivated at 37° C. for 24 hours. The cultured medium was smeared onto MRS agar plate and left at 37° C. for 3 days. After the incubation, colonies appeared on the agar medium were collected to be examined about bacterial features such as Gram staining pattern, glycolytic capacity and the like as illustrated below. As a result, the bacterium separated above was identified to be a *Lactobacillus* sp. strain.

Example 2

Purification of Lactic Bacteria from Patients' Feces Administering the Above *Lactobacillus* sp.

In order to investigate the compatibility and the antibacterial property of lactic bacteria separated in Example 1 to human inner body, 5 patients with chronic gastritis and enteritis were administered. Precisely, 100 ml of the above lactic bacteria was eaten respectively for 2 months in the state of an empty stomach, 30 minutes before rising in the morning and sleeping in the evening. As a result, the progress was improved before and after by injecting for 1 month and after injecting for 2 months, all the patients present in the experiment were recovered.

At this point, lactic bacteria were separated again from 5 administered patients' feces by the procedures described in Example 1 and thus $3~5 \times 10^{7cfu}/g$ of cells were obtained. Then the bacterial features were investigated to identify the lactic bacteria comparing with the bacteria separated in Example 1 and identical to that of the administered lactic bacteria separated in Example 1. Hence, the lactic bacteria have been named concisely with CSK 01.

The above lactic bacterium CSK 01 was lyophilized in the state of culture broth adding 10% skim milk, stored at −20° C. and then applied to various experiments for examining bacterial features.

Example 3

Gram Staining of Lactic Bacterium CSK 01

Figure 1B:

The bacterial features of CSK 01 were examined by using Gram staining. As a result, it was indicated to Gram positive as shown in FIG. 1*a* and FIG. 1*b* and identified to a rod without spores and in the size of 1.0~1.5 μm, which was a typical feature indicated in lactic bacillus, *Lactobacillus* sp.

Then, the lactic bacterium CSK 01 was investigated to elucidate the cultural properties. As a result, it made ash-colored colonies with 2~3 mm diameter onto MRS agar plate and can be cultivated preferably at 37° C. than at 30° C.

Example 4

Analysis of the CSK 01 Strain with API KIT 50 CHL

The CSK 01 strain was cultivated onto MRS agar plate at 37° C. for 48 hours in the anaerobic condition and suspended with suspension medium in the same turbidity with McFarland 2. Then the cultured cells were inoculated into API 50 CHL strip tube and covered the upper layer with mineral oil in order to examine 49 kinds of glycolytic capacity.

The glycolytic patterns were compared by analyzing the components in the standard *Lactobacillus rhamnosus* strain and the CSK 01 strain. As a result, in the standard *Lactobacillus rhamnosus* strain, β-gentiobiose and gluconate were included both in 85% and in the CSK 01 strain, 5% and 45% respectively.

Then, the glycolytic patterns were also examined by analyzing the components in the standard *Lactobacillus paracasei* subsp. *paracasei* strain and the CSK 01 strain of the present invention. As a result, in the *Lactobacillus paracasei* subsp. *paracasei* strain, 85% of α-methyl-d-glucoside, 99% of amygdaline, 93% of saccharose, 85% of β-gentiobiose and 85% of gluconate were included so as to be determined as positive and in the CSK 01 strain, 40%, 40%, 45%, 50% and 45% were included respectively so as to be decided negative.

Figure 2:
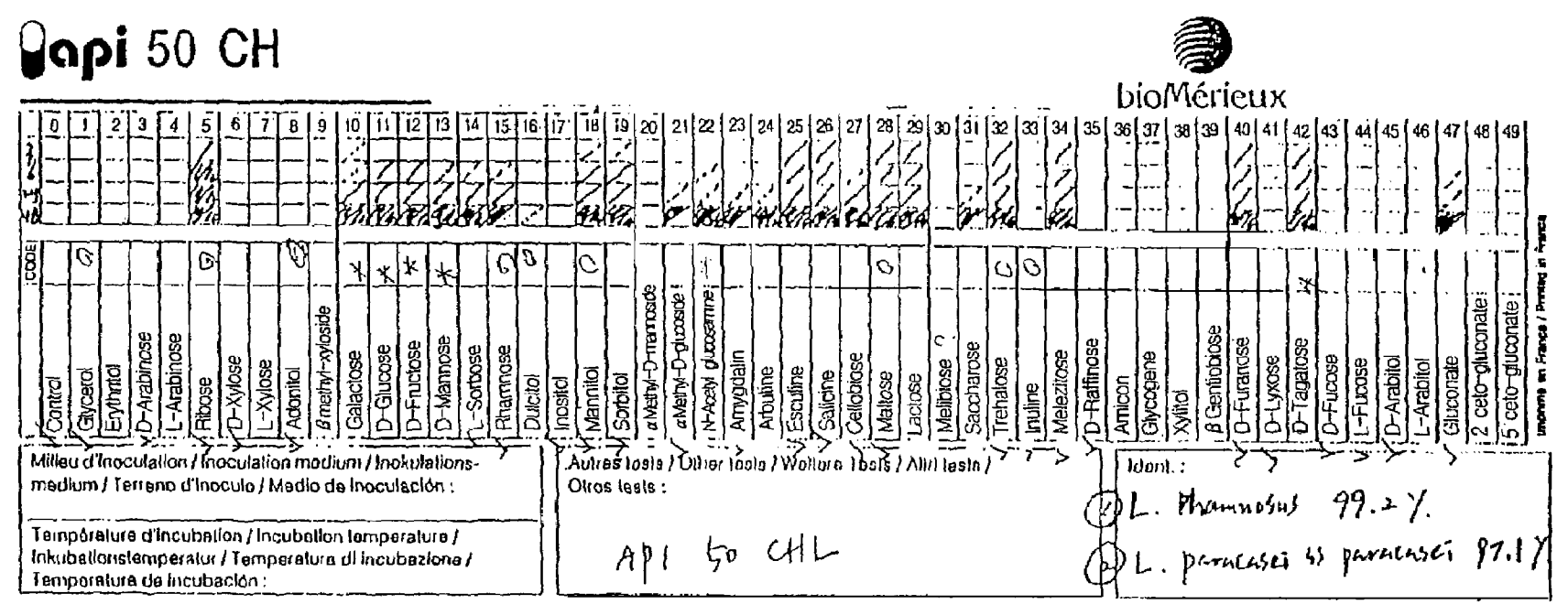

In addition, the glycolytic capacities were analyzed by using API identification software program. Consequently, the CSK 01 strain was shown to be similar in the glycolytic pattern to *Lactobacillus rhamnosus* and *Lactobacillus paracasei* subsp. *paracasei*, with 99.2% and 97.1% respectively as illustrated in FIG. 2.

Example 5

Analysis of Cellular Fatty Acid Composition

The CSK 01 strain was cultivated onto MRS agar plate at 37° C. for 48 hours and about 50 mg of culture broth (water-containing weight) was allotted to dry-cleaned teflon-lined screw cap tube with 13×100 mm of size. Then 1 ml of reagent 1 was added for performing the saponification at 100° C. for 30 minutes and 2 ml of reagent 2 was added for performing the methylation at 80° C. for 10 minutes. Again, 1.25 ml of reagent 3 was used to extract fatty acids and left at room temperature. Once 2 layers of reacted mixture were separated, the lower layer was removed and 3 ml of reagent 4 was added so as to wash with base for 5 minutes. Then, about two third of supernatant was moved to septum capped sample vial (12×32 mm; Alltech Associates, Inc., Illinois, USA) and utilized as an experimental sample.

Reagents (1) Reagent 1 (Saponification Reagent)

150 ml of ion-removed distilled water was mixed with 150 ml of methanol and then 45 g of NaOH (ACS authorization) was added and dissolved completely for the preparation of the saponification reagent.

(2) Reagent 2 (Methylation Reagent)

325 ml of 6.00 N HCl was mixed with 275 ml of methanol (reagent grade) for the preparation of the methylation reagent.

(3) Reagent 3 (Extraction Solvent)

200 ml of hexane (HPLC grade) was mixed with 200 ml of methyl tertiary butyl ether for the preparation of the extraction solvent.

(4) Reagent 4 (Base Wash)

10.8 g of NaOH (ACS authorization) was dissolved with 900 ml of ion-removed distilled water for the preparation of the base wash.

In order to analyze the composition of fatty acids as described in Example 5, Hewlett Packard series II gas chromatography model 6890 (Microbial ID, Inc., Delaware, USA) was used and methyl silica fused silica capillary column (HP 19091B-1020) with 25 ml×0.22 mm×0.33 m of size was exploited for the separation column.

Besides, microbial identification system software (Microbial ID, Inc., Delaware, USA) was utilized for the FAMEs profile. Then, the identification of peaks, the retention time and the area ratio of peaks were measured by comparing with those of standard calibration solution (Microbial ID., Delaware, USA).

At that time, the gas chromatography was performed in the condition as follows: carrier gas, hydrogen; column head pressure, 10 psi; spilt ratio, 100:1; spilt vent, 50 ml/min; septum purge, 5 ml/min; FID hydrogen, 30 ml/min; FID nitrogen, 30 ml/min; FID air, 400 ml/min; initial temperature, 170° C.; program rate, 5° C./min; final temperature, 270° C.; FID temperature, 300° C.; injection port, 250° C.; and injection volume, 2 μl.

Figure 3:
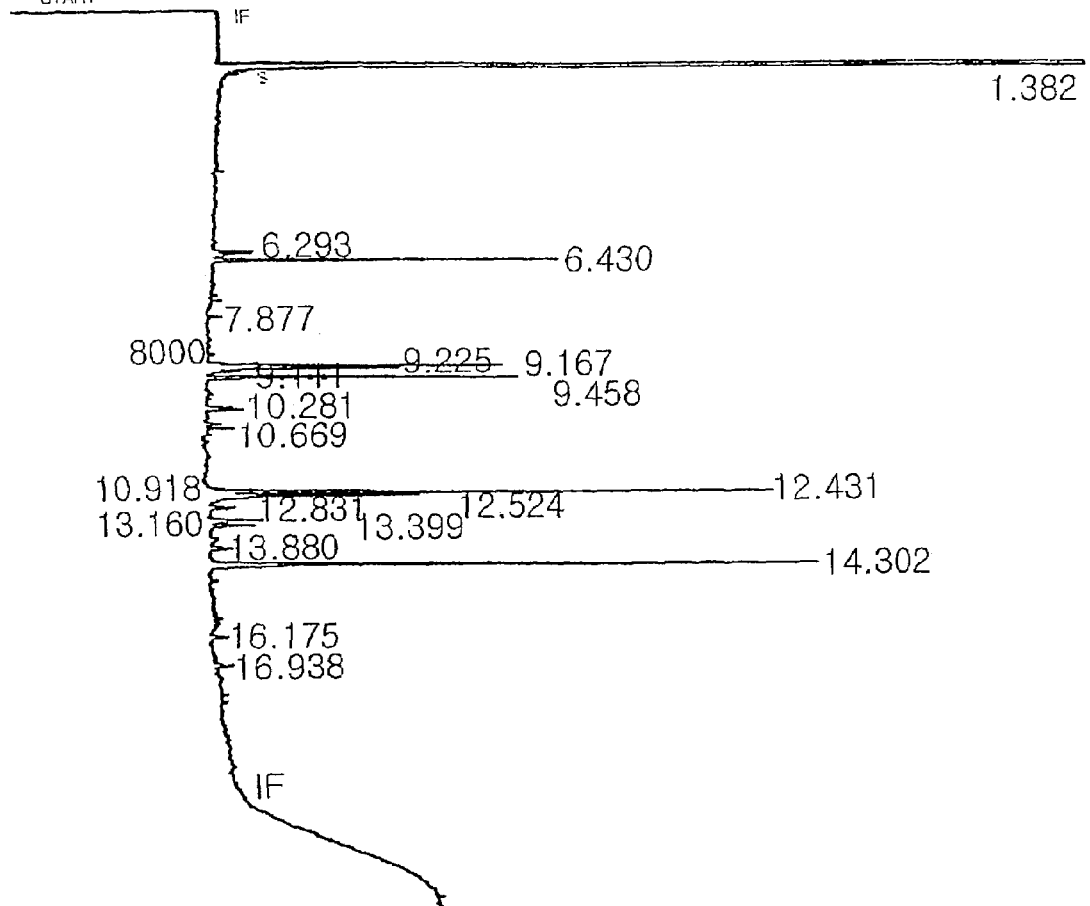
FIG. 3 depicts fatty acid compositions of said lactic bacterium by performing the automated gas chromatography with microbial identification system (Microbial ID. Inc., Newark, Del., USA)

As depicted in FIG. 3 and FIG. 4, the results of MIS gas chromatography were shown as followed; major fatty acids, $C_{16:0}$, sum in feature 7 ($C_{18:1\ w7c}$), $C_{18:1\ w9c}$, sum in feature 9 ($C_{19:0\ cyclo\ w10c}$) etc. As a result, the lactic bacterium of the present invention was identified to belong to *Lactobacillus* sp.

Example 6

BIOLOG Analysis by Metabolic Fingerprint

The CSK 01 strain was cultivated at 28~35° C. for 24 hours by using Biolog lactic acid bacteria agar (BLA) medium (Cat. #70004) and suspended with 20 ml of 0.85% NaCl so as to be adjusted in 35~42% range of optical density at 590 nm. Then 150 μl of the culture broth was allotted into 96 wells of Biolog GP microplate (Biolog Cat. #1004) respectively and cultivated at 28~35° C. for 24 hours.

The reactions were measured with the reader after incubated for 4 and 24 hours independently and analyzed to detect 95 carbon sources usage pattern with the micro release 3.50 software.

The above BIOLOG system was an automated system which can be applied to identify and classify microorganisms by analyzing the 95 carbon sources usage. Especially, it has been exploited to identify and classify lactic bacteria such as *Lactobacillus* sp., *Lactococcus* sp. and *Pediococcus* sp. As described above, the metabolic properties of the CSK 01 strain was characterized by using the carbon sources usage pattern. Consequently, the CSK 01 strain was identified to be *Lactobacillus rhamnosus* or *Lactobacillus paracasei* subsp. *paracasei* as depicted in FIG. 5a, FIG. 5b, FIG. 5c and FIG. 5d.

Example 7

(7-1) Extraction of Total Genomic DNA

Chromosomal DNA was separated by performing Hunter's method (1985) in the experimental strain and the standard strain. Namely, the preserved strain was inoculated to 10 ml of medium, incubated at 37° C. for 2~3 days and then cultivated with 100 ml of medium until reached the late exponential stage. About 5 g of bacterial debris was again treated with 10 ml of TE buffer containing 10 mg of lysozyme so as to be suspended for cell lysis at 30° C. for 2~3 hours.

The lysed cell solution was mixed with 1 ml of 20% SDS slowly and 1.5 ml of 5M NaCl and phenol were added so as to be shaked for 20 minutes slowly. Then it was centrifuged at 3,500 rpm for 10 minutes in order to obtain the supernatant, which was mixed with same volume of chloroform so as to be shaked for 10 minutes slowly and transferred to 100 ml sterilized beaker and mixed with the same volume of isopropanol.

Then, the cell supernatant was left at room temperature for 5 minutes and chromosomal DNA formed between two layers was separated with yellow tips. The resulting DNA was dissolved in the small volume of TE buffer and 20 μg/ml of RNase was added and incubated at 50° C. for 1 hour. Again, 100 μg/ml of protease K, 100 mM of NaCl and 0.4% of SDS were mixed and reacted at 37° C. for 1 hour.

The procedures from the phenol treatment and TE buffer addition were repeated and DNA concentrations were measured with the absorbance at 260 nm.

(7-2) 16S rRNA Sequencing Analysis

Genomic DNA of the experimental strain was assayed quantitatively in the above stage and exploited to perform the polymerase chain reaction (PCR).

At that time, chromosomal DNA of *Lactobacillus* sp. separated before and demonstrated Table 1 was utilized in 10 μg/ml of concentration as a template for performing the PCR.

TABLE 1

Standard lactic bacteria used for the identification of the CSK 01 strain

| standard strains | accession numbers |
|---|---|
| *Lactobacillus paracasei* | ATCC 11582 |
| *Lactobacillus paracasei* | ATCC 11974 |
| *Lactobacillus paracasei* | ATCC 25302 |
| *Lactobacillus paracasei* | ATCC 25598 |
| *Lactobacillus paracasei* | ATCC 25599 |
| *Lactobacillus paracasei* | ATCC 27092 |
| *Lactobacillus paracasei* | ATCC 27216 |
| *Lactobacillus paracasei* | ATCC 29599 |
| *Lactobacillus rhamnosus* | ATCC 7469 |
| *Lactobacillus rhamnosus* | ATCC 9595 |
| *Lactobacillus rhamnosus* | ATCC 10863 |
| *Lactobacillus rhamnosus* | ATCC 11981 |
| *Lactobacillus rhamnosus* | ATCC 15820 |
| *Lactobacillus rhamnosus* | ATCC 21052 |

The compositions of PCR reaction mixture were as followed: in 100 µl of the total volume, 1× reaction buffer consisted in 100 mM Tris-HCl (pH 8.3), 500 mM of KCl, 2 mM of MgCl$_2$, 0.2 mM of dNTP, 200 pmol of sense primer F9 with SEQ ID NO: 1 , 200 pmol of antisense primer 1542R with SEQ ID NO: 2 and 2.5 unit of Taq polymerase as illustrated in Table 2.

TABLE 2

Primers for 16S rRNA sequencing analysis of lactic bacteria in the present invention

| primers | | nucleotide sequences |
|---|---|---|
| 16S | Y2 | 5'-CCCACTGCTGCCTCCCGTAGGAGT-3' |
| | para | 5'-CACCGAGATTCAACATGG-3' |

The PCR procedures were performed in the reaction condition as followed: denaturation at 95° C. for 5 minutes, again denaturation at 95° C. for 1 minute, annealing at 60° C. for 1 minute, extension at 72° C. for 2 minutes and this process was repeated 30 cycles. Finally, post-extension was proceeded at 72° C. for 10 minutes and the reaction mixture was preserved at 15° C.

The PCR products were separated by using 1% agarose gel electrophoresis and stained with ethidium bromide for the identification.

The PCR product of 1500 bp size was presumed and eluted from the agarose gel by using Qiaquick gel extraction kit (Qiagen) and then cloned into pGEM-T easy vector to construct the LA1500/pGEM-T vector.

Then 16S rRNA sequencing analysis was accomplished by using 16S DNA (position 9-1542) of the CSK 01 strain and PCR. Precisely, the PCR product of about 1500 bp size was cloned into the pGEM-T easy vector and its nucleotide sequence was determined.

In order to determine the nucleotide sequence of the gene, the vector LA1500/pGEM-T was separated by using Wizard™ plus Midipreps DNA Purification System (Promega) and the LA 1500 bp fragment was examined in Bionex Corporation by using automated sequence analyzer (ALFexpress™; Pharmacia Biotech). As a result, the nucleotide sequence of 16S DNA was shown in SEQ ID NO: 3 of Sequence List and FIG. 6.

Example 8

Analysis of Nucleotide Sequence Data with BLAST

The above nucleotide sequence of 16S rRNA was examined and compared with those from already-known Lactobacillus sp. strains and other representative strains belonging to different families by using BLAST program (Altschul et al., 1990; http//www.ncbi.nih.Gov /BLAST) and their homologies were judged.

The family tree was manufactured by exploiting the neighbor-joining method and calculating distance values obtained from the BLAST software.

As a result, the 16S rRNA sequences of the CSK 01 strain were illustrated in FIG. 7 and on the basis of this molecular systematic classification, the CSK 01 strain of the present invention was proved to belong to Lactobacillus casei group. Especially, it showed the highest value of 99.9% homology with that of Lactobacillus paracasei (D79212).

Example 9

Multiplex RAPD PCR Analysis

In order to investigate the experimental strains, the random amplified polymorphic DNA polymerase chain reaction (RAPD PCR) which enabled the typings of Lactobacillus sp. to be analyzed was performed by using arbitrary primers with about 10 bp size.

In addition, the primers which can detect Lactobacillus paracasei specifically were prepared and then used to compare genes of the experimental strains with those of 8 Lactobacillus paracasei strains As demonstrated above, chromosomal DNA of Lactobacillus sp. with 10 µg/µl of concentration separated before was utilized as a template for performing the RAPD-PCR.

The compositions of PCR reaction mixture were as followed: in 50 µl of the total volume, 1×reaction buffer consisting in 100 mM Tris-HCl (pH 8.3), 500 mM of KCl, 3 mM of MgCl$_2$, 0.2 mM of dNTP, 10 pmol of RP primer with SEQ ID NO: 4, 10 pmol of CRA25 primer with SEQ ID NO: 5 and 1 unit of Taq polymerase as illustrated in Table 3.

TABLE 3

Primers for RAPD analysis of lactic bacteria in the present invention

| | Primers | nucleotide sequences |
|---|---|---|
| RAPD | RP | 5'-CAGCACCCAC-3' |
| | CRA25 | 5'-AACGCGCAAC-3' |

The PCR procedures were performed in the reaction condition as followed: at 94° C. for 3 minutes, at 45° C. for 45 seconds and at 72° C. for 1 minute (1 cycle); at 94° C. for 45 seconds, at 45° C. for 45 seconds and at 72° C. for 1 minute and this process was repeated 30 cycles; finally at 94° C. for 45 seconds, at 45° C. for 45 seconds and at 72° C. for 5 minutes (1 cycle). Then post-extension was proceeded at 72° C. for 8 minutes and the reaction mixture was preserved at 4° C.

The PCR products were separated by using 1.5% agarose gel electrophoresis and stained with ethidium bromide for typing band patterns.

According to the Ward method (1999), Lactobacillus paracasei group specific primers for detecting the specific sequences were prepared by referring 16S rRNA nucleotide sequences of Lactobacillus paracasei, Lactobacillus rhamnosus and the like.

Figure 8:
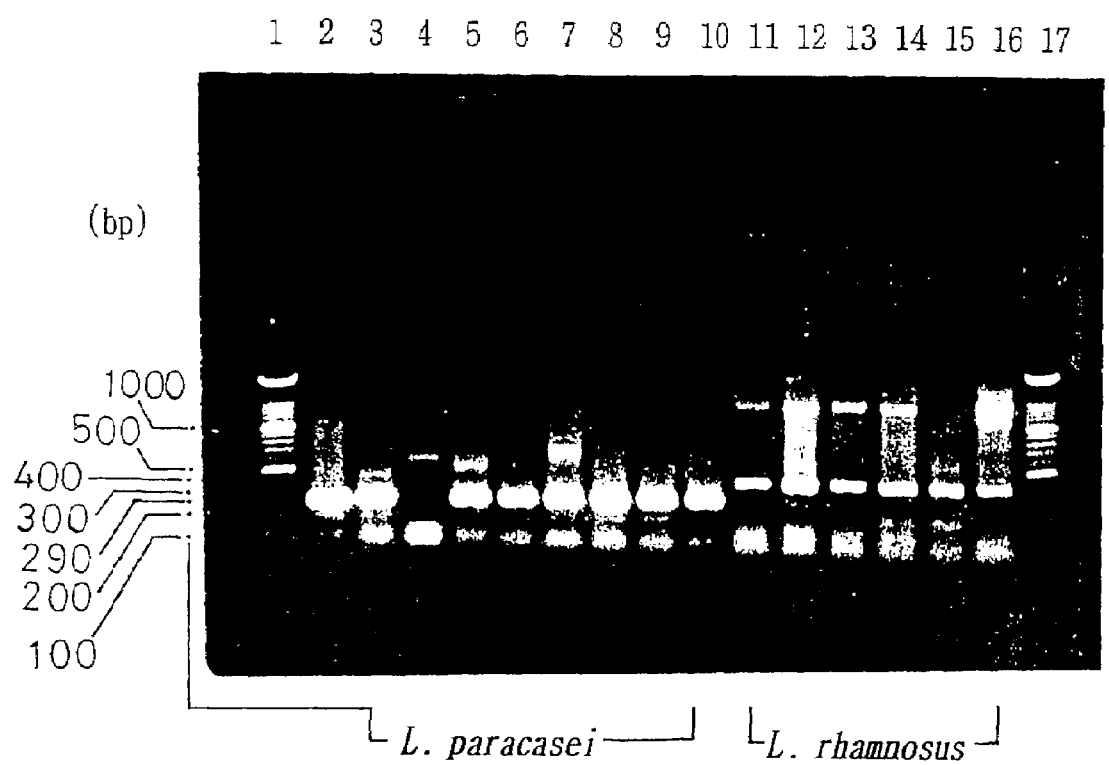
FIG. 8 depicts the PCR result of said lactic bacterium by using specific primers for *Lactobacillus paracasei* group, which are compared with those of standard *Lactobacillus* sp.

When the PCR was performed with primers containing unique nucleotide sequences of Lactobacillus paracasei, about 300 bp bands were detected both in the experimental strain and the standard Lactobacillus paracasei strain and the CSK 01 strain of the present invention was identified as a Lactobacillus paracasei subsp. paracasei as depicted in FIG. 8 (lane 1, 17:100 bp DNA ladder; lane 2: the experimental strain; lane 3~10: Lactobacillus paracasei; lane 11~16: Lactobacillus rhamnosus).

As illustrated in Example 3~9, the CSK 01 strain of the present invention was examined for biochemical properties, 16S rRNA sequencing, PCR analysis of identification and the like and as a result, it was proved to be a Lactobacillus paracasei subsp. paracasei.

Example 10

Comparation of DNA Nucleotide Sequences in the CSK 01 Strain and *Lactobacillus paracasei* Subsp. *paracasei*

The DNA nucleotide sequences of the CSK 01 strain and JCM 8130 strain were determined as depicted in FIG. 9. As a result, the nucleotide sequences were distinguished in No. 861 and No. 1451: in the CSK 01 strain, G and A respectively and in the JCM 8130 strain, T and G.

Example 11

RAPD PCR with RP Primer in the CSK 01 Strain and *Lactobacillus* Sp. Strain

Figure 10:
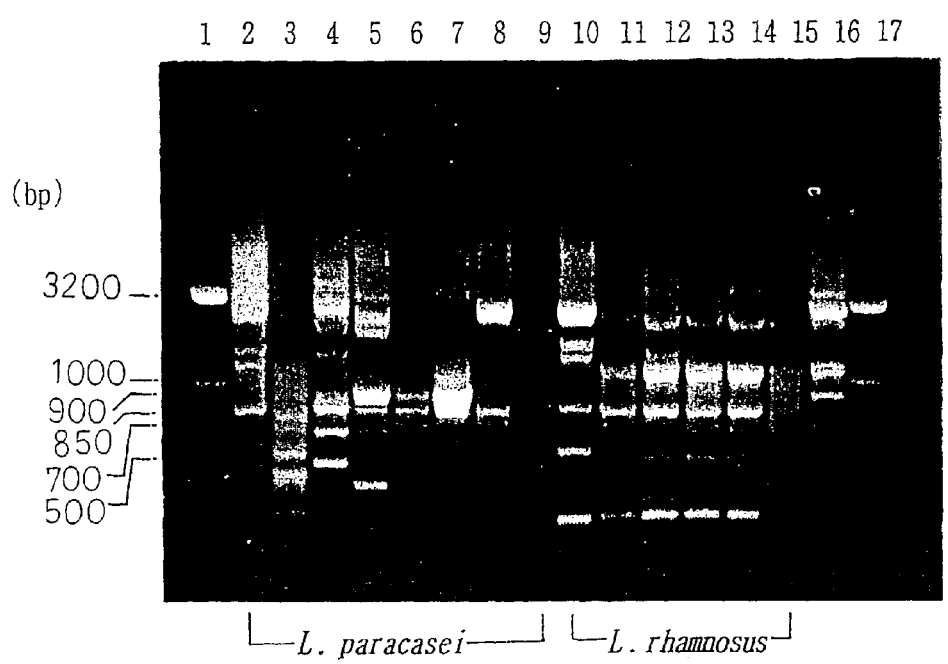
FIG. 10 depicts the RAPD PCR results of said lactic bacterium and the standard *Lactobacillus* sp. by using RP primer.

When the RAPD PCR was performed with RP primer, about 850 bp bands were detected both in the experimental strain and the standard *Lactobacillus paracasei* strain, which corresponded to the result obtained from the Ward method (1999). Thus the CSK 01 strain of the present invention was proved to be a *Lactobacillus paracasei* subsp. *paracasei* as depicted in FIG. 10 (lane 1, 17:100 bp DNA ladder; lane 2: the experimental strain; lane 3~10: *Lactobacillus paracasei*; lane 11~16: *Lactobacillus rhamnosus*). However, other bands except the 850 bp band had a disparable pattern from those of the standard strains, which showed the specificity for the CSK 01 strain.

Example 12

RAPD PCR with CRA25 Primer in the CSK 01 Strain and *Lactobacillus* Sp. Strain

Figure 11:
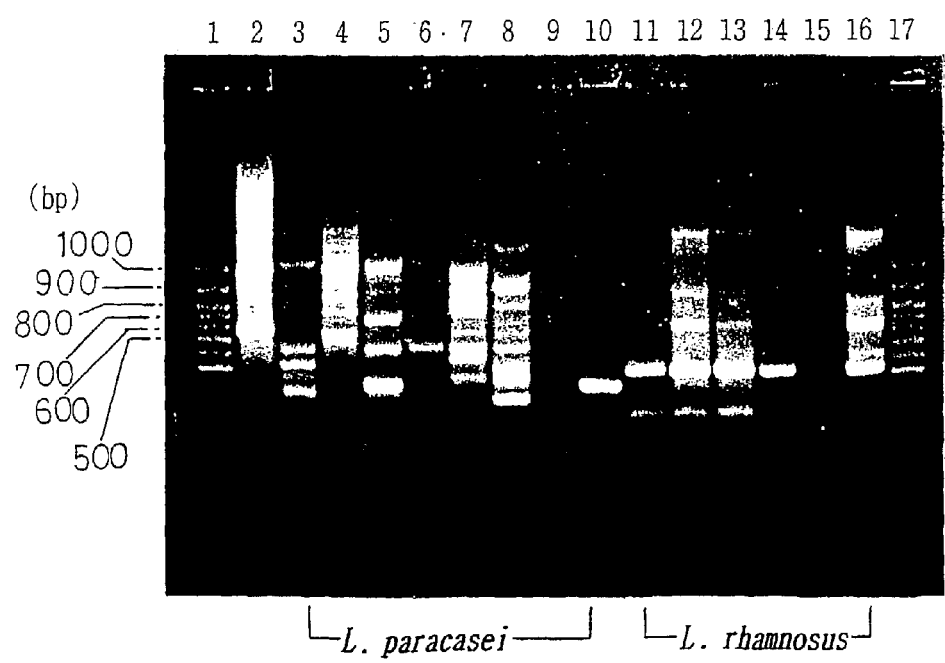
FIG. 11 depicts the RAPD PCR results of said lactic bacterium and the standard *Lactobacillus* sp. by using CRA25 primer.

When the RAPD PCR was performed with CRA25 primer, about 980 bp and 550 bp bands were not detected in the standard *Lactobacillus paracasei* strain, which was different from the CSK 01 strain of the present invention. The above result proved the specificity for the CSK 01 strain as depicted in FIG. 11 (lane 1, 17:100 bp DNA ladder; lane 2: the experimental strain; lane 3~10: *Lactobacillus paracasei*; lane 11~16: *Lactobacillus rhamnosus*).

As demonstrated in Example 10~12, in 16S rRNA sequencing and the PCR with RP and CRA25 primers, the CSK 01 strain of the present invention were recognized to have specific properties which did not correspond to those of conventional strains.

Example 13

Safety of the CSK 01 Strain to Balb/c Mouse

In order to examine the safety of the CSK 01 strain, Balb/c mice of 2-week age bred germ-free in *Medical Inspection of National Veterinary Science* were chosen. Concretely, the CSK 01 strain was inoculated into 10% skim milk ($5 \times 10^{9cfu}$/ml), administered with the proper amount 0.3 ml and its 2-fold amount 0.6 ml orally once a day for 10 days and after 2 months the safety was measured.

As a result, all the experimental groups injecting 0.3 ml and 0.6 ml of the culture broth were found to survive and be normal with the naked eye.

In the autopsy, the experimental group did not have differences of parenchymal organs (liver, heart, lung, kidney etc.) and digestive organs (stomach, small intestine and large intestine) from the standard group and all the organs were proved normal The muci of stomach, small intestine, large intestine in the administered group were smeared onto MRS agar plate and cultivated at 37° C. for 48 hours. As illustrated in Table 4, a large number of lactic bacteria were separated from the administered group but no lactic bacteria was detected in the standard group.

TABLE 4

Safty of lactic bacteria in the present invention

|  |  | the administered group | the standard group |
|---|---|---|---|
| administered amount |  | 0.3, 0.6 | — |
| No. of bacteria |  | $5 \times 10^{9cfu}$/g | — |
| No. |  | 20 | 10 |
| administering period |  | 10 days | — |
| results | safety examination | 10 days and then after 2 months | — |
|  | death | — | — |
|  | autopsy | *parenchymal organs: normal liver heart lung kidney *digestive organs: normal stomach small intestine large intestine | *parenchymal organs: normal liver heart lung kidney *digestive organs: normal stomach small intestine large intestine |
|  | recovery | innumerable bacteria in stomach, small and large intestine | — |

Example 14

Resistance to Acids in the CSK 01 Strain of the Present Invention

In order to prepare culture broth, 100 ml of 10% skim milk (pH 6.2) was mixed with 10 N HCl and pH was adjusted to 1.0, 1.5, 2.0, 2.5, 3.0, 3.5, 4.0 respectively. Then 1 ml of the CSK 01 culture solution ($5 \times 10^{9cfu}$/ml) was inoculated and cultivated for 4 days. The number of bacteria and pH in 2-day and 4-day culture media were measured and the results were summarized in Table 5.

In the case of pH 1.0 medium, the 2-day cultivation changed pH in the range of 1.0~0.84 and lactic bacteria were not separated.

In the case of pH 1.5 medium, the 2-day cultivation changed pH in the range of 1.5~2.0 and less than $10^{1cfu}$/ml of lactic bacteria were separated.

In the case of pH 2.0 medium, the 2-day cultivation changed pH in the range of 2.2~2.5 and $10^{4~5cfu}$/ml of lactic bacteria were separated and in the case of pH 2.5 medium, the 2-day cultivation changed pH in the range of 2.7~3.0 and $10^{3~6cfu}$/ml of lactic bacteria were separated.

In the case of pH 3.0 medium, the 2-day cultivation changed pH in the range of 3.4~3.6 and $10^{6~7cfu}$/ml of lactic bacteria were separated.

In the case of pH 3.5 medium, the 2-day cultivation changed pH in the range of 3.6~3.7 and $10^{7~8cfu}$/ml of lactic bacteria were separated.

In the case of pH 4.0 medium, the 2-day cultivation changed pH in the range of 4.5~5.0 and more than $10^{8cfu}$/ml of lactic bacteria were separated.

In the cases of the 4-day cultivation according to pH, the numbers of lactic bacteria were similar to those of the 2-day cultivations.

TABLE 5

Resistance to acids in the CSK 01 strain

| pH (100 ml of 10% skim milk) | No. of samples | 2-day culture | | 4-day culture | |
|---|---|---|---|---|---|
| | | pH | No. of cells ($^{cfu}$/ml) | PH | No. of cells ($^{cfu}$/ml) |
| 1.0 | 5 | 0.84~1.0 | — | 0.8~0.9 | — |
| 1.5 | 5 | 1.5~2.0 | 10~50 | 1.3~1.6 | 10~30 |
| 2.0 | 5 | 2.2~2.5 | $10^{4-5}$ | 2.2~2.6 | $10^{4-5}$ |
| 2.5 | 5 | 2.7~3.0 | $10^{5-6}$ | 2.7~3.1 | $10^{5-6}$ |
| 3.0 | 5 | 3.4~3.6 | $10^{6-7}$ | 3.5~3.6 | $10^{6-7}$ |
| 3.5 | 5 | 3.6~3.7 | $10^{7-8}$ | 3.6~4.0 | $10^{7-8}$ |
| 4.0 | 5 | 4.5~5.0 | more than $10^8$ | 4.6~5.0 | more than $10^8$ |
| Std. (6.0) | 5 | 5.8~5.9 | $7 \times 10^9$ | 5.7~5.9 | $7 \times 10^9$ |

Example 15

Resistance to Bilis in the CSK 01 Strain

In order to investigate the resistance to bilis of the CSK 01 strain, 100 ml of 10% skim milk was adjusted with porcine bilis (Sig B8631) to 1.0, 1.5, 2.0, 2.5, 3.0, 3.5, 4.0 and 4.5% concentration and then 1 ml ($5\times10^{9cfu}$/ml) of the CSK 01 culture solution was inoculated and cultivated for 2 days and 4 days. Then the culture solution was diluted with MRS broth stored at 4° C. gradually in 10× and 1 ml of diluted solution was smeared onto plates for measuring the cell number.

The number of bacteria was in the range of $10^{7-9cfu}$/ml when bilis was added with 1.0, 1.5, 2.0 and 2.5% respectively, $10^{5-6cfu}$/ml when bilis was added with 3.0 and 3.5% and reduced to less than $10^{2-3cfu}$/ml when bilis was added with 4.0 and 4.5%, which proved the resistance to bilis of the CSK 01 strain.

According to the ratio of bilis amount, the results of 4-day cultivation was similar to those of 2-day cultivation as depicted in Table 6.

TABLE 6

Resistance to bilis of lactic bacteria in the present invention

| bilis (%) | No. of samples | No. of cells ($^{cfu}$/ml) | |
|---|---|---|---|
| | | 2-day culture | 4-day culture |
| 1.0 | 5 | more than $10^9$ | more than $10^9$ |
| 1.5 | 5 | more than $10^9$ | more than $10^9$ |
| 2.0 | 5 | $10^8$ and more | $10^7$ and more |
| 2.5 | 5 | $10^7$ and more | $10^6$ and more |
| 3.0 | 5 | $10^6$ and more | $10^5$ and more |
| 3.5 | 5 | $10^5$ and more | $10^4$ and more |
| 4.0 | 5 | $10^3$ and more | $10^3$ and more |
| 4.5 | 5 | $10^2$ and more | $10^2$ and more |
| STD | 5 | more than $5 \times 10^9$ | more than $5 \times 10^9$ |

Example 16

Attachment to and Proliferation on Gastric Mucus of Balb/c Mice in the CSK 01 Strain In order to examine the attachment and proliferation of the CSK 01 strain, 20 heads of Balb/c mouse of 2-week age bred germ-free in *Medical Inspection of National Veterinary Science* were utilized. Concretely, the culture solution of the CSK 01 strain was administered in 0.3 ml amount ($7\times10^{9cfu}$/ml) orally for 10 days once a day after cultivated for 48 hours.

After administered for 2 months, stomachs of mouse were picked out for obtaining gastric mucous and 1 g of gastric mucus was diluted gradually with MRS broth stored at 4° C. in 10×. Then, 1 ml of the diluted solution was smeared onto MRS agar plate and cultivated at 37° C. for 48 hours so as to adjust the number of cells to $7\times10^{8cfu}$/ml., in order to observe with the scanning electron microscopy (SEM), part of stomach was cut and washed with 1 M phosphate buffered saline (PBS; pH 7.2~7.4) rapidly and then fixed with 2~3% glutaraldehyde in 0.1 M PBS, stored at 4° C. for 2~3 hours, washed with the same buffer, post-fixed with 1% osmium tetroxide in 0.1 ml PBS at 4° C. for 2 hours and then dehydrated with ethanol 50, 70, 80, 90% for 5 minutes and 100% for 20 minutes orderly.

Figure 12A:
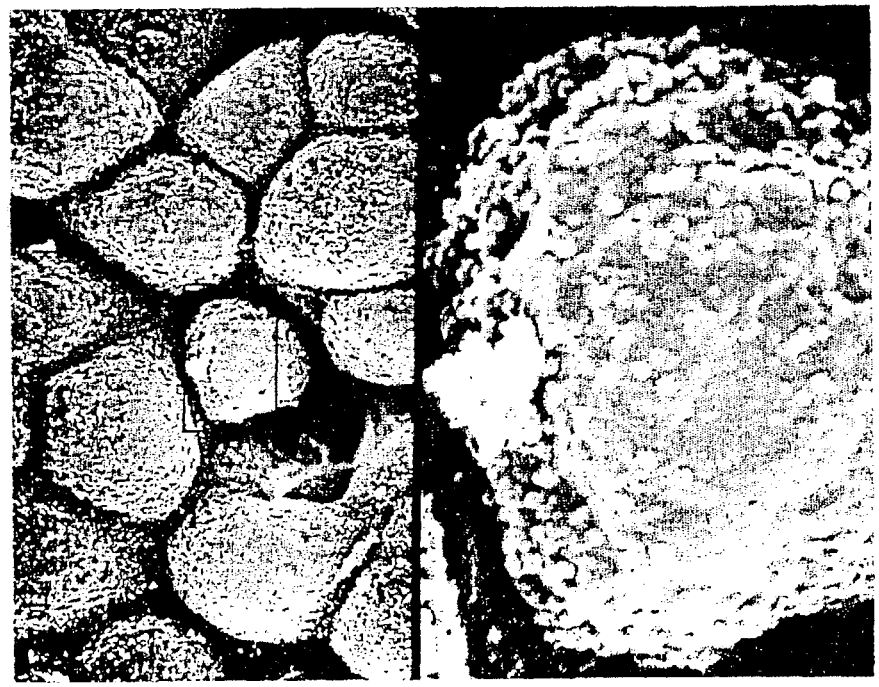
FIG. 12a and FIG. 12b depicts the properties of said lactic bacterium which can attach to and proliferate on gastric mucus.
Figure 12B:
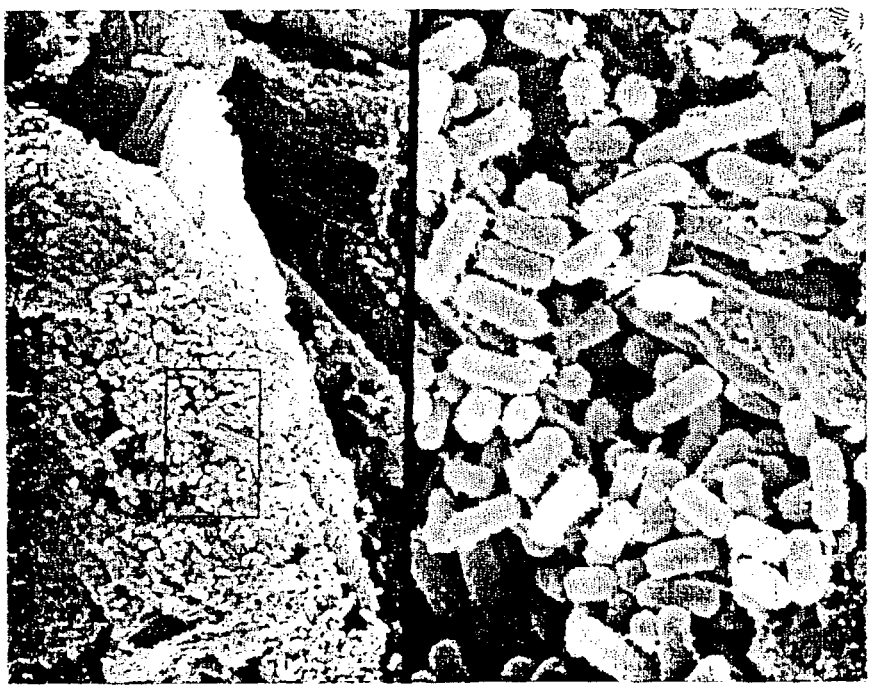

Then, as a substituting agent, isoamyl acetate was used, dried with the critical point dryer and coated with ions in order to be observed with the electron microscopy (Hitach, S-570). As a result, the CSK 01 strain was confirmed to attach to and proliferate on gastric mucus as depicted in FIG. 12*a* and FIG. 12*b*.

Example 17

Attachment to and Proliferation on Small Intestinal Mucus of Balb/c Mice in the CSK 01 Strain In order to investigate the attachment to and proliferation on small intestinal mucus, the CSK 01 strain was separated from gastric mucous as described above and observed with the electron microscopy.

Figure 13A:
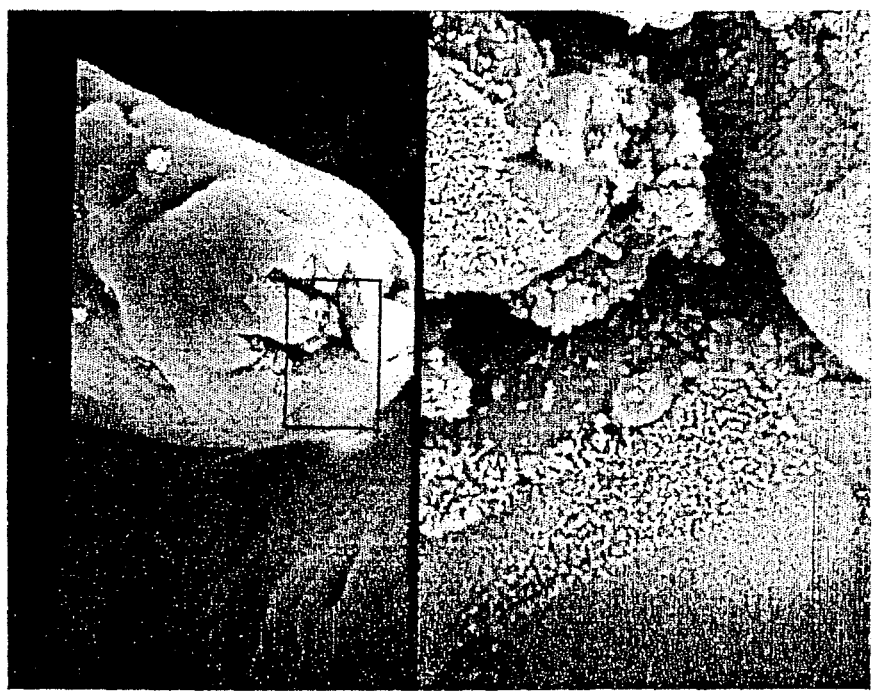
FIG. 13a and FIG. 13b depicts the properties of said lactic bacterium which can attach to and proliferate on small intestinal mucus.
Figure 13B:

As a result, the CSK 01 strain was obtained with the number of $3\times10^{6cfu}$ and confirmed to attach to and proliferate on gastric mucus by the electron microscopic observation as depicted in FIG. 13*a* and FIG. 13*b*.

As demonstrated in Example 13~17, the CSK 01 strain of the present invention was proved to be resistant to acids and bilis and attach to and proliferate on gastric mucus and intestinal mucus of Balb/c mice.

Example 18

Infectivity of *Helicobacter pyroli* Against Balb/c Mice

*Helicobacter pylori* was obtained from patients and stored in Department of Microbiology, Bokeum hospital, Pusan. Precisely, *Helicobacter pylori* 121 strain was lotted out.

The *Helicobacter pylori* was cultivated in the anaerobic condition (gas packed jar) with Mueller—Hinton broth (MHB) containing 10% calf serum for 4 days and then smeared onto 10% sheep blood medium to be incubated again for 4 days. Thus, it was identified to be Gram-positive, flexible and spiral and harvested by using 10% Mueller—Hinton broth stored at 4° C. and glass beads. Then the cells were administered orally to Balb/c mice once a day for 5 days in 0.3 ml of culture solution with $2 \times 10^{9cfu}$/ml and after 3 days stomachs of Balb/c mice were cut.

1 g of gastric mucus was diluted with MHB stored at 4° C. in 10× gradually and 1 ml of diluted solution was smeared onto 10% sheep blood medium. As a result, $7 \times 10^{7cfu}$/g of bacteria were separated.

Figure 14:
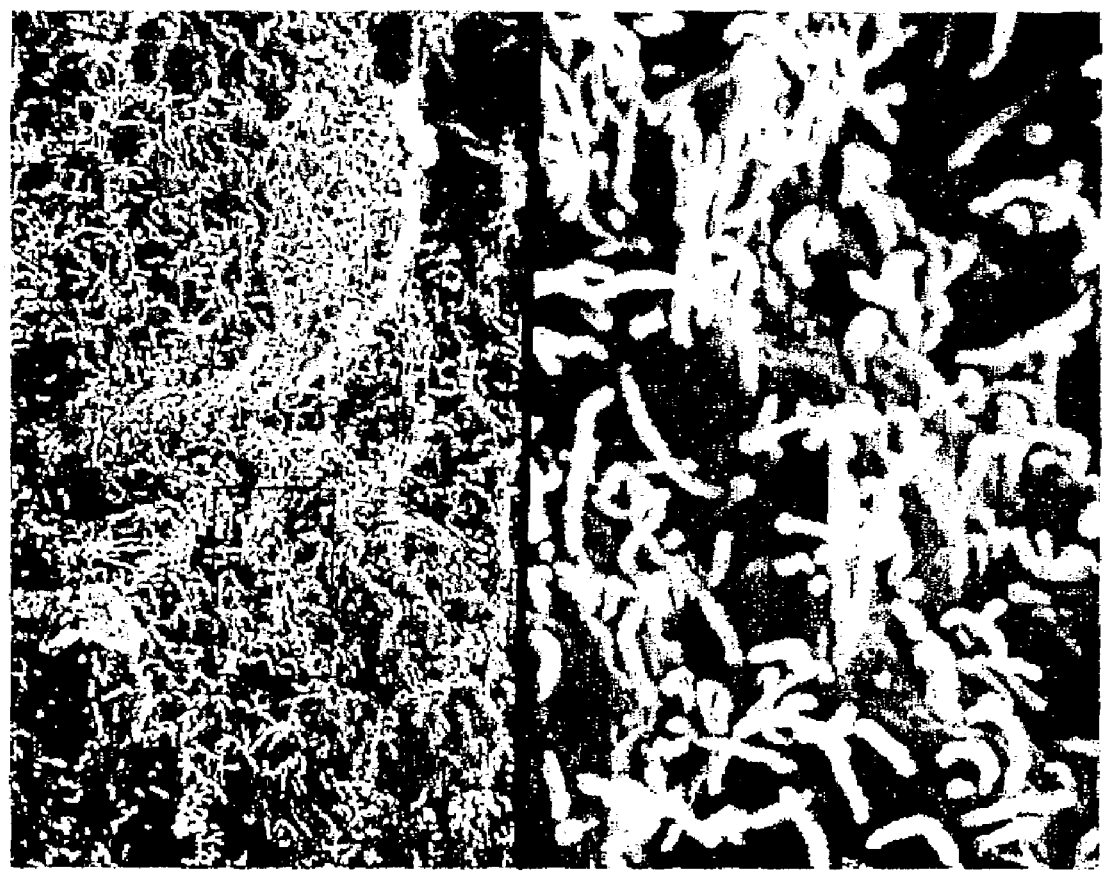
FIG. 14 depicts the infection of *Helicobacter pylori* onto the gastric mucus of Balb/c mouse.

In addition, tissues treated as above was observed with the electron microscopy and examined to be infected with a large number of bacteria as shown in FIG. 14.

Example 19

Killing effect of the CSK 01 Strain Against *Helicobacter pylori* Infected in Balb/c Mice Balb/c mice infected with *Helicobacter pylori* were administered orally with the culture broth of the CSK 01 strain ($5 \times 10^{9cfu}$/ml) once a day in 0.3 ml amount for 10 days and after 2 months, gastric mucus was investigated to detect *Helicobacter pylori* by using the previously described method. As result, *Helicobacter pylori* was not found and the CSK 01 strain was detected with $1 \times 10^{9cfu}$/g.

Figure 15:
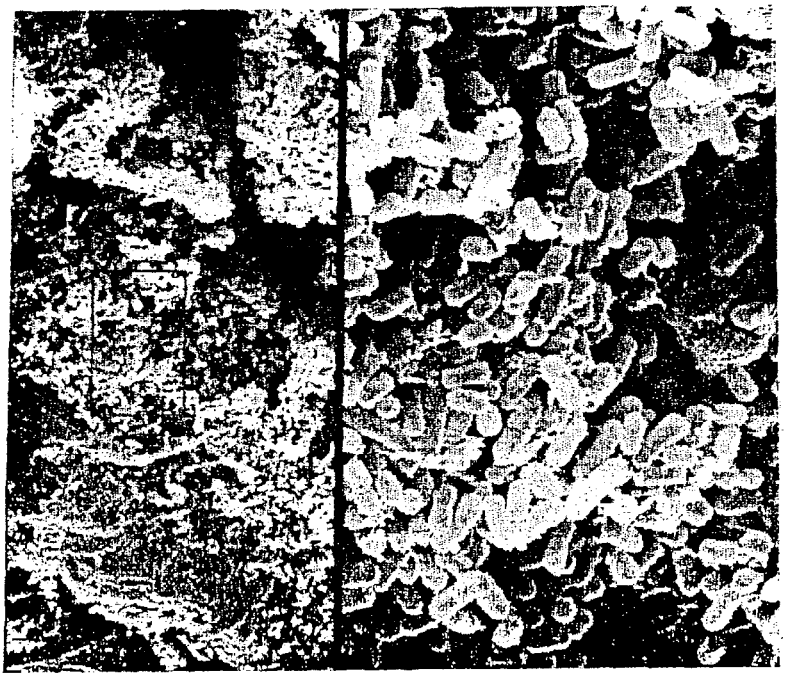
FIG. 15 depicts the killing effects of said lactic bacterium upon *Helicobacter pylori* in infected Balb/c mice.

In addition, the gastric mucus treated above was observed with the electron microscopy and examined to be infected with a large number of the administered bacteria but *Helicobacter pylori* was not found as shown in FIG. 15.

Example 20

Killing Effect of Antibacterial Substance from the CSK 01 Strain against *Helicobacter pyroli*

The culture broth of the CSK 01 strain was cultivated with 10% skim milk at 37° C. for 48 hours and 100 ml of the culture broth was allotted in 50 ml amount to the sonicator and maintained at 4° C. for 30 seconds. This procedure was repeated 5 times with sonicating (Sonical material, Vcx375) and then centrifuged at 10,000 g for 30 minutes so as to recover the supernatant.

Then, 80% saturated solution of ammonium sulfate was added to float cells, left at 4° C. for 24 hours and centrifuged so as to recover the precipitates. Then, the cells were diluted 2 times with sterilized distilled water stored at 4° C. and poured onto dialysis membrane (PGC 29-0593-37, MWCO, 10K) so as to be dialyzed at 4° C. for 48 hours by using distilled water.

Then the purified solution prepared above was allotted again with saturated 40% ammonium sulfate solution, left at 4° C. for 24 hours and centrifuged at 10,000 G for recovering the supernatant. Again it was diluted 2 times with the same process and freeze-dried at 4° C. for 48 hours.

The lyophilized antibacterial substance of the CSK 01 strain was re-diluted 2 times after 10% skim milk was added, sonicated and centrifuged at 10,000 G to obtain supernatants.

Figure 16:
FIG. 16 depicts the killing effects of antibacterial substance purified from said lactic bacterium upon *Helicobacter pylori*.

The culture broth of *Helicobacter pylori* was smeared onto Mueller—Hinton agar containing 10% calf serum and a disk absorbing the antibacterial substance of the present invention was placed in the center of culture plate and incubated in the anaerobic condition. As a result the inhibition range was measured and the proliferation of *Helicobacter pylori* was verified to suppressed completely around the disk as depicted in FIG. 16.

Example 21

Infectivity of *Escherichia coli* 0157:H7 Against Intestinal Mucus of Balb/c Mice

*Escherichia coli* 0157/H7 strain was allotted from Microbiology Lab., Department of Veterinary Science, Kyungsang University.

*Escherichia coli* 0157/H7 strain was inoculated onto BHI broth, cultivated at 37° C. for 18 hours and harvested by adding sterilized physiological saline on the agar plate and using glass beads. Then the number of cells was calculated by diluting gradually with the sterilized physiological saline in 10× and to be $3 \times 10^{9cfu}$/ml.

The culture medium was administered orally into Balb/c mice in 0.3 ml amount once a day for 5 days and after 3 days, small intestinal mucus was cut partially.

1 g of small intestinal mucus was diluted gradually in 10× by adding sterilized physiological saline and then 1 ml of diluted solution was smeared onto 7% sheep blood medium and cultivated at 37° C. for 18 hours. As a result, cells in $6 \times 10^{5cfu}$/g was separated and confirmed to be Gram negative, rod shaped, to react positive against *E. coli* 0157:H7 antiserum and the like so as to be a *Escherichia coli*.

Figure 17:
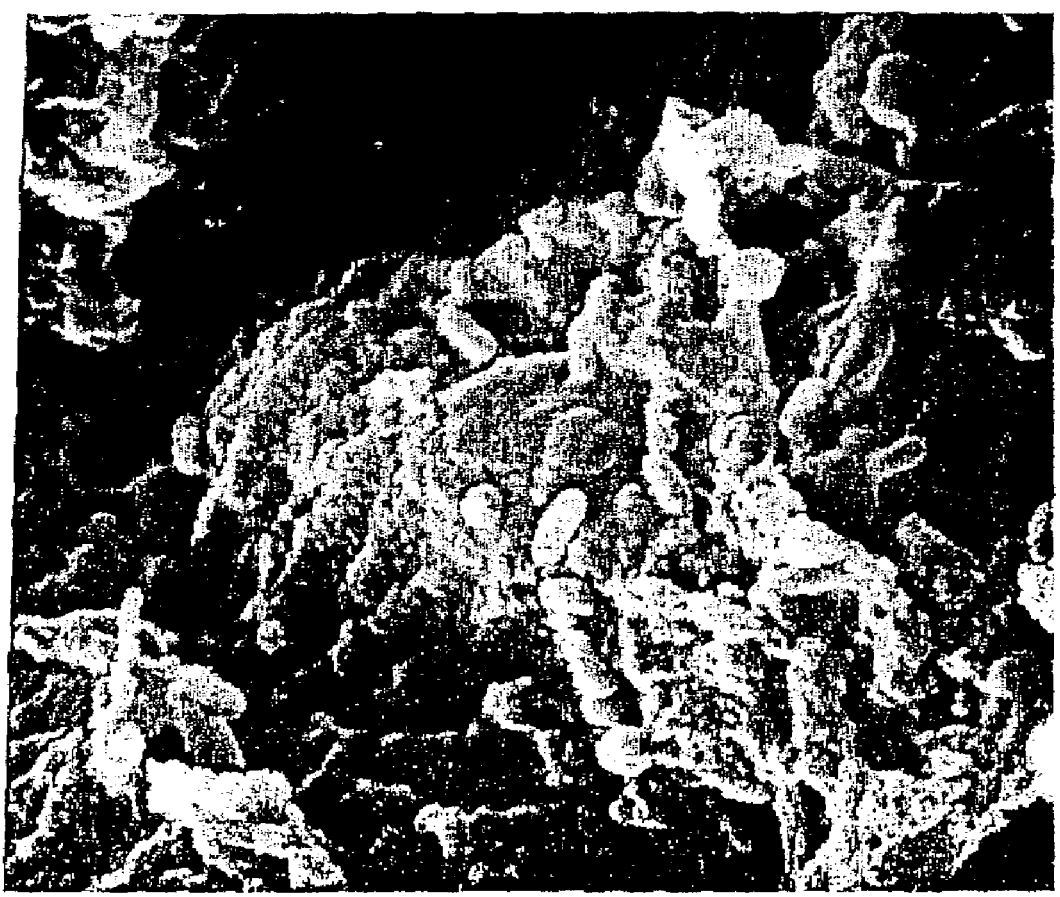
FIG. 17 depicts the infection of *Escherichia coli* 0157:H7 onto the small intestinal mucus of Balb/c mouse.

On the other hand, the small intestinal mucus was observed with the electron microscopy to find the survival of *Escherichia coli* and a large number of *Escherichia coli* was confirmed to attach to and proliferate on the mucus as shown in FIG. 17.

Example 22

Killing Effect of the CSK 01 Strain Against *Escherichia coli* 0157:H7 Infected Balb/c Mice Balb/c mice infected with *Escherichia coli* 0157:H7 were administered orally with the culture broth of the CSK 01 strain ($5 \times 10^{9cfu}$/ml) once a day for 10 days and after 2 months, small intestinal mucus was investigated to detect *Escherichia coli* 0157:H7 with the electron microscopy.

Concretely, 1 g of small intestinal mucus was diluted gradually in 10× by adding sterilized physiological saline and 1 ml of the diluted solution was smeared onto BHI agar plate and cultivated at 37° C. for 20 hours in order to examine the survival of bacteria. As a result, *Escherichia coli* 0157:H7 was not found and the CSK 01 strain was detected in $4 \times 10^{5cfu}$/g when the same procedure with the above was performed.

Figure 18:
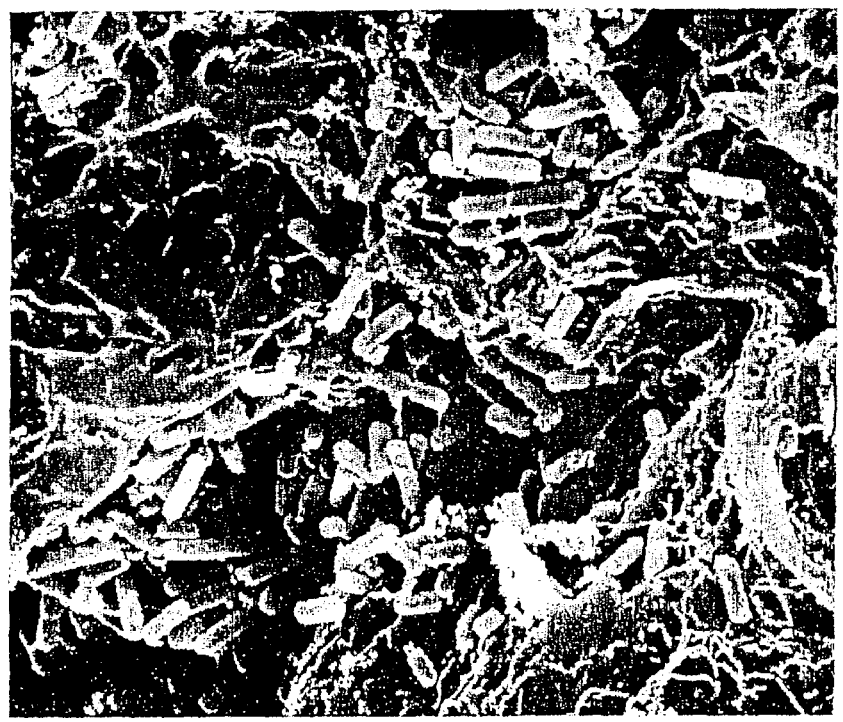
FIG. 18 depicts the killing effect of said lactic bacterium upon *Escherichia coli* 0157:H7 in the infected Balb/c mouse.

Meanwhile, the small intestinal mucus treated above was observed with the electron microscopy again. As a result, it was verified to be infected only with a large number of the administered the CSK 01 strain and *Escherichia coli* 0157:H7 was not found at all as shown in FIG. 18.

Example 23

Killing Effect against *Escherichia coli* in the Mixed Culture of the CSK 01 Strain and *Escherichia coli* 0157:H7

1 ml of the CSK 01 strain ($2 \sim 6 \times 10^{8cfu}$) in MRS broth and 1 ml of *E. coli* ($2 \sim 6 \times 10^{8cfu}$) in BHI broth were adjusted to have the same concentrations of cells. Both were inoculated into 10% skim milk together, cultivated at 37° C. for 5 days and after 20 hours the numbers of the CSK 01 cell and *E. coli* were calculated.

Concretely, the CSK 01 strain was estimated by using MRS agar medium and *E. coli*, by using MacConkey agar medium and 1 ml of the culture broths were smeared onto agar plates respectively to get the cell numbers.

Figure 19:
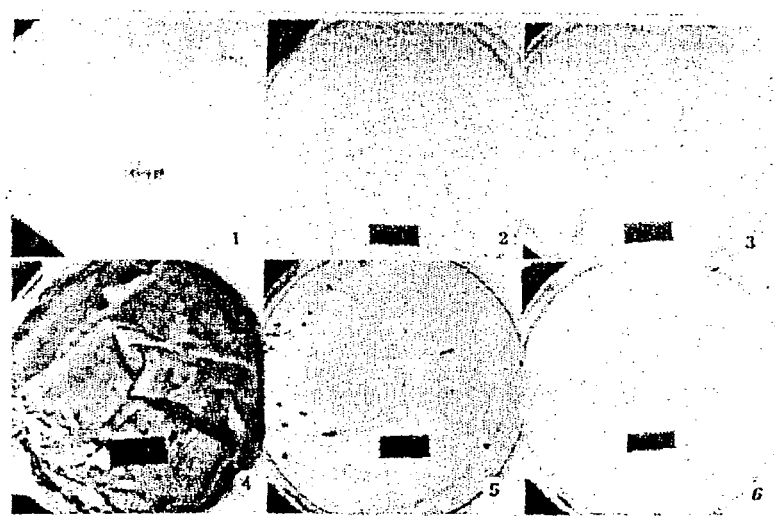
FIG. 19 depicts the killing effect upon *Escherichia coli* in the mixed culture of said lactic bacterium and *E. coli* 0157:H7.

As a result, the number of *E. coli* was examined to reduce from after 30 hours, then most of cells were killed after 40 hours and finally all the cells died killed after 70 hours as depicted FIG. 19.

Contrarily, the CSK 01 strain was not varied in the number of cells ($4 \times 10^{9 cfu}$/ml) even after 70 hours.

Example 24

Killing Effect of Antibacterial Substance from the CSK 01 Strain Against *Escherichia coli*

The antibacterial substance was purified, precipitated with saturated ammonium sulfate solution, freeze-dried as described above, diluted to 300 mg/ml and absorbed into a disk in 20 μl amount.

Figure 20:
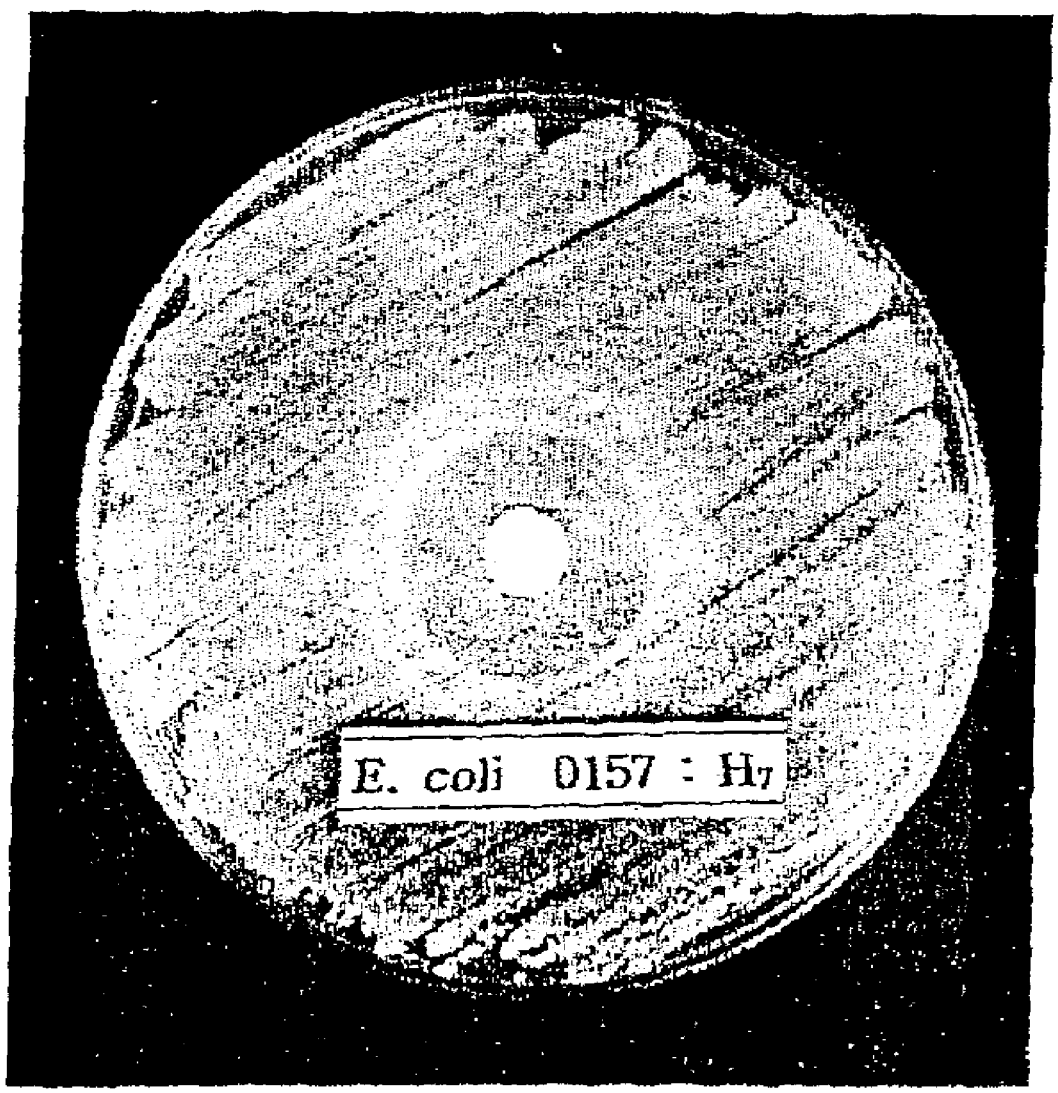
FIG. 20 depicts the killing effect of the antibacterial substance from said lactic bacterium upon *Escherichia coli* 0157:H7.

*E. coli* cells cultivated in BHI broth were smeared onto the tryptic soy agar plate and the disk-absorbing the antibacterial substance was left in the center of plate, then incubated at 37° C. for 24 hours. As a result, it was confirmed that the proliferation of *E. coli* was inhibited around the disk as depicted in FIG. 20.

As demonstrated in Example 18~24, the CSK 01 strain of the present invention was proved to have the antibacterial properties for killing *Helicobacter pyroli* inducing gastritis of Balb/c mice and *Escherichia coli* inducing enteritis.

INDUSTRIAL APPLICABILITY

As illustrated above, the present invention relates to novel *Lactobacillus paracasei* strain (*Lactobacillus paracasei* subsp. *paracasei* CSK 0) which is prepared by the process; separating lactic bacteria from gastric mucosa; administering them to gastritis and enteritis patients; and separating again from the recovered patients' feces. The *Lactobacillus* strain of the present invention can attach to and proliferate on gastric and intestinal mucosa, resist to acidic and bilious conditions outstandingly and have excellent antibacterial properties, especially against *Helicobacter pylori*. Therefore, the *Lactobacillus* strain and its antibacterial substance are expected to be applied to various fields efficiently.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. *Lactobacillus paracasei* subsp. *paracasei* CSK 01 strain having an antibacterial property wherein said *Lactobacillus paracasei* subsp. *paracesi* is the deposited strain of Accession Number: KCTC 0907 BP.

2. The *Lactobacillus paracasei* subsp. *paracasei* CSK 01 strain of claim 1, wherein the antibacterial property is against *Helicobacter pylori* and *Escherichia coli* O157:H7.

3. The *Lactobacillus paracasei* subsp. *paracasei* CSK 01 strain of claim 1, being resistant to acids and bilis and which can attach to and proliferate on gastric mucus and intestinal mucus.

4. A food composition comprising the *Lactobacillus* strain of claim 1 as an effective component in combination with a food, the *Lactobacillus* strain having functions of preventing and treating gastritis, gastric ulcer and duodenitis induced by *Helicobacter pylori* and enteritis, colitis and rectitis induced by *Escherichia coli* and other intestinal pathological bacteria.

5. A pharmaceutical composition comprising the *Lactobacillus* strain of claim 1 as an effective component in combination with a pharmaceutical carrier, the *Lactobacillus* strain having functions of preventing and treating gastritis, gastric ulcer and duodenitis induced by *Helicobacter pylori* and enteritis, colitis and rectitis induced by *Escherichia coli* and other intestinal pathological bacteria.

* * * * *